US008840871B2

(12) United States Patent
Wei et al.

(10) Patent No.: US 8,840,871 B2
(45) Date of Patent: Sep. 23, 2014

(54) MULTIPHASE PERSONAL CARE COMPOSITION WITH ENHANCED DEPOSITION

(75) Inventors: Karl Shiqing Wei, Mason, OH (US); Qing Stella, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 440 days.

(21) Appl. No.: 12/510,880

(22) Filed: Jul. 28, 2009

(65) Prior Publication Data

US 2010/0158830 A1 Jun. 24, 2010

Related U.S. Application Data

(60) Provisional application No. 61/084,146, filed on Jul. 28, 2008.

(51) Int. Cl.
*A61K 8/03* (2006.01)
*A61K 8/73* (2006.01)

(52) U.S. Cl.
USPC .......................... 424/78.03; 424/713; 424/59

(58) Field of Classification Search
CPC ...................................................... A61K 8/064
See application file for complete search history.

(56) References Cited

U.S. PATENT DOCUMENTS

| | | | |
|---|---|---|---|
| 2,438,091 | A | 3/1948 | Lynch |
| 2,528,378 | A | 10/1950 | Mannheimer |
| 2,658,072 | A | 11/1953 | Kosmin |
| 3,929,678 | A | 12/1975 | Laughlin et al. |
| 5,037,818 | A | 8/1991 | Sime |
| 5,487,884 | A | 1/1996 | Bissett et al. |
| 5,543,074 | A | 8/1996 | Hague et al. |
| 5,652,228 | A | 7/1997 | Bissett |
| 5,674,511 | A | 10/1997 | Kacher et al. |
| 5,681,852 | A | 10/1997 | Bissett |
| 5,688,752 | A | 11/1997 | Turner |
| 5,756,436 | A | 5/1998 | Royce et al. |
| 5,804,540 | A | 9/1998 | Tsaur et al. |
| 6,004,544 | A | 12/1999 | Schrader et al. |
| 6,033,680 | A | 3/2000 | Dixon et al. |
| 6,126,954 | A | 10/2000 | Tsaur |
| 6,136,765 | A | 10/2000 | Glenn, Jr. et al. |
| 6,146,660 | A | 11/2000 | Terren et al. |
| 6,156,713 | A | 12/2000 | Chopra et al. |
| 6,213,166 | B1 | 4/2001 | Thibiant et al. |
| 6,255,264 | B1 | 7/2001 | Fleurot et al. |
| 6,348,188 | B1 | 2/2002 | Eccleson et al. |
| 6,383,999 | B1 | 5/2002 | Coyle et al. |
| 6,395,691 | B1 | 5/2002 | Tsaur |
| 6,495,151 | B2 | 12/2002 | McAtee |
| 6,506,369 | B2 | 1/2003 | Ambler et al. |
| 6,534,456 | B2 | 3/2003 | Hayward et al. |
| 6,569,438 | B1 | 5/2003 | Banowski et al. |
| 6,645,511 | B2 | 11/2003 | Aronson et al. |
| 6,699,488 | B2 | 3/2004 | Deckner |
| 6,716,440 | B2 | 4/2004 | Aronson |
| 6,759,376 | B2 | 7/2004 | Zhang et al. |
| 6,780,826 | B2 | 8/2004 | Zhang et al. |
| 6,849,584 | B2 | 2/2005 | Geary et al. |
| 6,923,975 | B2 | 8/2005 | Aronson |
| 6,930,078 | B2 | 8/2005 | Wells et al. |
| 6,936,265 | B2 | 8/2005 | Bleckman et al. |
| 6,955,817 | B2 | 10/2005 | McAtee |
| 7,073,965 | B2 | 7/2006 | Look et al. |
| 7,192,598 | B2 | 3/2007 | Aronson |
| 7,202,199 | B2 | 4/2007 | Shiloach et al. |
| 7,208,168 | B2 | 4/2007 | Fleissman et al. |
| 7,326,671 | B2 | 2/2008 | Shiloach et al. |
| 7,527,077 | B2 | 5/2009 | McCall |
| 7,560,125 | B2 | 7/2009 | Ananthapadmanabhan et al. |
| 7,666,825 | B2 | 2/2010 | Wagner |
| 7,671,007 | B2 | 3/2010 | Carnali et al. |
| 7,700,528 | B2 | 4/2010 | Wei et al. |
| 7,776,346 | B2 | 8/2010 | O'Connor et al. |
| 7,776,347 | B2 | 8/2010 | Kerschner et al. |
| 7,853,422 | B2 | 12/2010 | Sasaki |
| 7,867,962 | B2 | 1/2011 | Wei et al. |
| 7,875,582 | B2 | 1/2011 | Pham et al. |
| 7,954,392 | B2 | 6/2011 | Belcher |

(Continued)

FOREIGN PATENT DOCUMENTS

EP   0103911 A1 * 3/1984 ............... A61K 9/10
EP   0817608 B1   12/2000

(Continued)

OTHER PUBLICATIONS

Burgess, D. J., Practical Analysis of Complex Coacervate Systems, 140 (1) J. of Colloid and Interface Science, 227, 227-238, (Nov. 1990).
Caelles, J., et al., Anionic and Cationic Compounds in Mixed Systems, *106 Cosmetics & Toiletries 49*, 49-54 (Apr. 1991).
Griffin, W.C., Classification of Surface Active Agents by "HLB", *J. Soc. Cosmetic Chemists*, 311, 311-326 (1949).
I. J. Lin, Hydrophile-lipophile balance (hlb) of fluorocarbon surfactants and its relation to the critical micelle concentration (cmc) 76 (14) *J. Phys. Chem.* 2019, 2019-2023 (1972).
van Oss, C. J. *Coacervation, Complex-Coacervation and Flocculation*, 9 J. Dispersion Science and Tech., 561, 561-573, (1988-89).
International Search Report dated Apr. 6, 2010, PCT/IB2009/053283.
International Search Report PCT/US2009/051969 dated Feb. 20, 2012, 4 pages.

(Continued)

*Primary Examiner* — Sue Liu
*Assistant Examiner* — Jessica Kassa

(57) ABSTRACT

A multiphase personal care composition that comprises a structured surfactant phase and an oil continuous benefit phase. The structured surfactant phase comprises from about 5% to about 30% of a mixture of lathering surfactants, a lamellar inducing agent and a cationic polymer. The oil continuous benefit phase comprises a hydrocarbon based benefit material and a low HLB emulsifier. The low HLB emulsifier comprises an unsaturated monoglyceryl ester having from about 14 to about 30 carbon atoms. The oil continuous benefit phase comprises a ratio of said hydrocarbon based benefit materials to said low HLB emulsifier comprising from about 30:1 to about 200:1.

19 Claims, 3 Drawing Sheets

(56) References Cited

U.S. PATENT DOCUMENTS

| | | |
|---|---|---|
| 2002/0012646 A1 | 1/2002 | Royce et al. |
| 2002/0045941 A1 | 4/2002 | Ishikubo et al. |
| 2002/0102295 A1 | 8/2002 | Niemiec |
| 2002/0155077 A1 | 10/2002 | Galante et al. |
| 2003/0108507 A1 | 6/2003 | Clipson et al. |
| 2004/0017728 A1 | 1/2004 | Becker et al. |
| 2004/0057920 A1 | 3/2004 | Focht |
| 2004/0157754 A1 | 8/2004 | Geary et al. |
| 2004/0195519 A1 | 10/2004 | Refregier et al. |
| 2004/0219119 A1 | 11/2004 | Wei et al. |
| 2004/0223991 A1 | 11/2004 | Wei et al. |
| 2004/0223992 A1 | 11/2004 | Clapp et al. |
| 2004/0234470 A1 | 11/2004 | Zhang et al. |
| 2004/0248748 A1* | 12/2004 | Wei et al. .............. 510/130 |
| 2005/0220735 A1 | 10/2005 | Tsaur et al. |
| 2005/0220736 A1 | 10/2005 | Polonka et al. |
| 2005/0238680 A1 | 10/2005 | Stella |
| 2006/0079419 A1 | 4/2006 | Wagner et al. |
| 2006/0182699 A1 | 8/2006 | Taylor et al. |
| 2006/0251606 A1 | 11/2006 | Coffindaffer et al. |
| 2006/0252662 A1 | 11/2006 | Soffin et al. |
| 2007/0020691 A1 | 1/2007 | Kanter et al. |
| 2007/0027050 A1 | 2/2007 | Crotty et al. |
| 2007/0059263 A1 | 3/2007 | Taniguchi et al. |
| 2007/0167338 A1 | 7/2007 | McHugh et al. |
| 2007/0212323 A1 | 9/2007 | Polonka et al. |
| 2007/0288186 A1 | 12/2007 | Datta et al. |
| 2008/0031845 A1 | 2/2008 | Stella et al. |
| 2008/0050320 A1 | 2/2008 | Haskel et al. |

FOREIGN PATENT DOCUMENTS

| | | |
|---|---|---|
| EP | 1195154 A2 | 6/2002 |
| EP | 1176941 A1 | 12/2005 |
| JP | 2005089337 A | 4/2005 |
| WO | WO 92/12911 | 8/1992 |
| WO | WO 95/26710 A1 | 10/1995 |
| WO | WO 99/38491 | 8/1999 |
| WO | WO 01/30308 | 5/2001 |
| WO | WO 01/70923 | 9/2001 |
| WO | WO 02/42740 | 5/2002 |
| WO | WO 2004/100919 A1 | 11/2004 |

OTHER PUBLICATIONS

International Search Report PCT/US2009/051969 including the Written Opinion of the International Searching Authority dated Feb. 20, 2012, 9 pages.

* cited by examiner

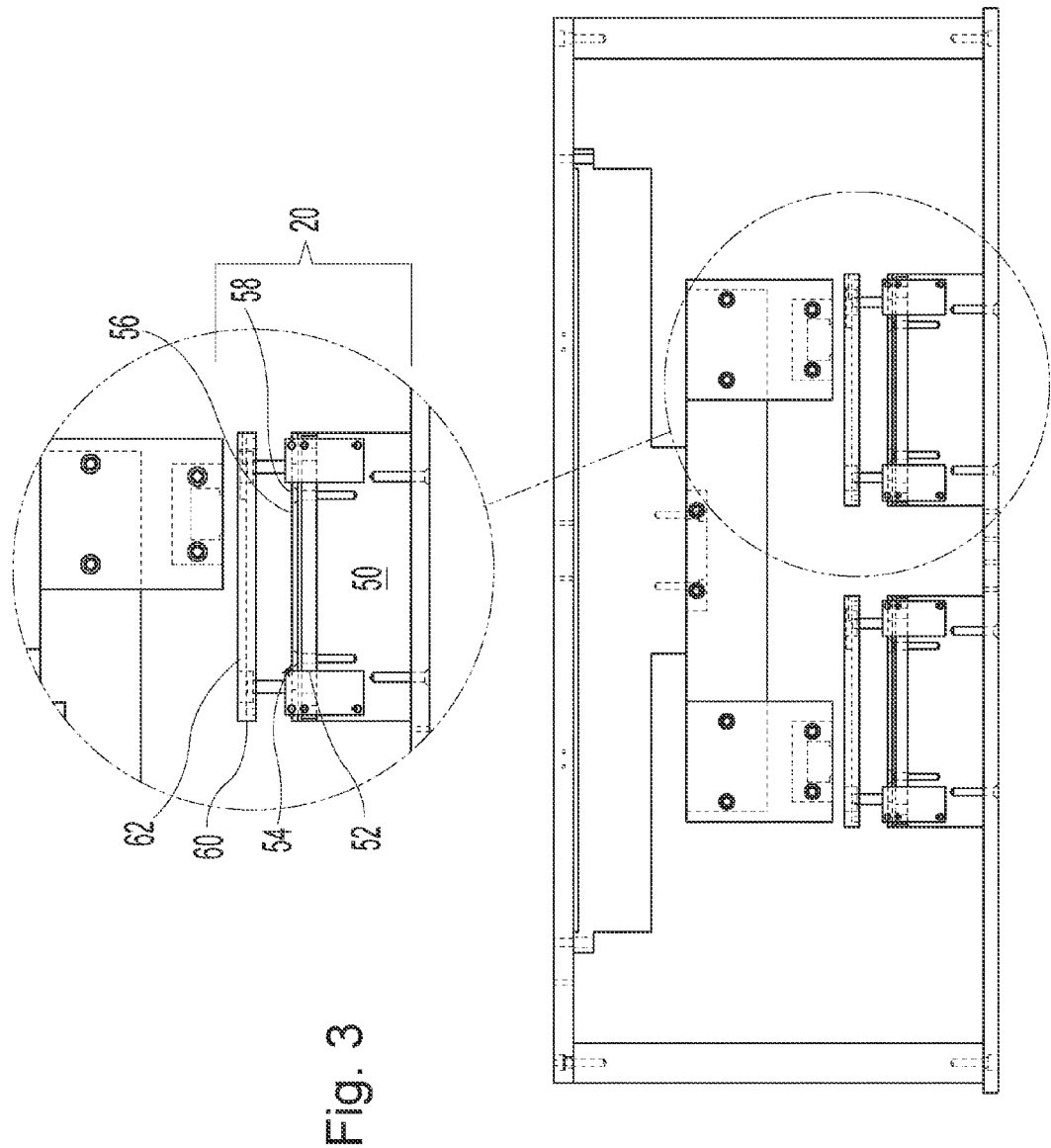

MULTIPHASE PERSONAL CARE COMPOSITION WITH ENHANCED DEPOSITION

CROSS REFERENCE TO RELATED APPLICATION

This application claims the benefit of U.S. Provisional Application No. 61/084,146, filed Jul. 28, 2008.

FIELD OF THE INVENTION

The present invention relates to a multiphase personal care composition that comprises a structured surfactant phase and an oil continuous benefit phase comprising a ratio of hydrocarbon based benefit materials to low HLB emulsifier that ranges from about 30:1 to about 200:1.

BACKGROUND OF THE INVENTION

Many commercially available personal care compositions attempt to provide skin-conditioning benefits. These personal care compositions are aqueous systems that comprise benefit agents in combination with surfactants. Although these personal care compositions provide both conditioning and cleansing benefits, it is often difficult to formulate a product that deposits sufficient amount of benefit agents on the skin during use. The low deposition of the personal care composition is caused by the interaction of the benefit agents and the surfactants within the personal care composition. Generally, the benefit agents are emulsified by the surfactant leaving only a small amount of benefit agents available for deposition.

Several approaches have been taken to combat the emulsification of the benefit agents by surfactants in personal care compositions. One approach is to raise the rheology of the benefit agents; however, the increased rheology negatively impacts the skin feel due to the tackiness of the benefit agents. Another approach is to add large amounts of benefit agents to the personal care compositions. In some instances, the raised level of benefit agents negatively affects the stability of the personal care compositions, as well as, the speed of lather generation, the total lather volume and the overall product performance. A third approach is to add cationic polymer to the personal care composition. Generally, the addition of the cationic polymer does not increase deposition of the benefit agent due to the competing mechanisms of the cationic polymer and the benefit agent.

Accordingly, there is an unmet need for a stable multiphase personal care composition that provides significantly enhanced benefit agent deposition without negatively impacting lather performance and after-use skin feel. It is the object of present invention to fulfill this unmet need.

SUMMARY OF THE INVENTION

The present invention, one embodiment relates to a multiphase personal care composition that comprises a structured surfactant phase and an oil continuous benefit phase. The structured surfactant phase comprises from about 5% to about 30% of a mixture of lathering surfactants, a lamellar phase inducing agent and a cationic deposition polymer. The oil continuous benefit phase comprises a hydrocarbon based benefit material and a low HLB emulsifier. The low HLB emulsifier comprises an unsaturated monoglyceryl ester having about 14 to about 30 carbon atoms. The oil continuous benefit phase comprises a ratio of the hydrocarbon based benefit materials and a low HLB emulsifier comprises from about 30:1 to about 200:1.

The present invention, in another embodiment, relates to a multiphase personal care composition that comprises a structured surfactant phase and an oil continuous benefit phase. The structured surfactant phase comprises from about 5% to about 30% of a mixture of lathering surfactants, a lamellar phase inducing agent and a cationic deposition polymer. The mixture of lathering surfactants is selected from anionic surfactants, nonionic surfactants, amphoteric surfactants, cationic surfactants and mixtures thereof. The cationic polymer comprises an average molecular weight of greater than about 100,000 to greater than about 400,000 and a charge density of greater than about 0.2 meq/gram to greater than about 0.4 meq/gram. The oil continuous benefit phase comprises a hydrocarbon based benefit material and a low HLB emulsifier. The low HLB emulsifier comprises an unsaturated monoglyceryl ester having about 14 to about 30 carbon atoms. The oil continuous benefit phase comprises a ratio of the hydrocarbon based benefit materials and a low HLB emulsifier comprises from about 30:1 to about 200:1.

The present invention, in another embodiment, relates to a multiphase personal care composition that comprises a structured surfactant phase and an oil continuous benefit phase. The structured surfactant phase comprises from about 15% to about 22% of a mixture of lathering surfactants, a lamellar phase inducing agent and a cationic deposition polymer. The mixture of the lathering surfactants comprises an anionic surfactant, a nonionic surfactant and an amphoteric surfactant. The lamellar phase inducing agent comprises an electrolyte. The cationic polymer is selected from cationic guar, cationic guar derivatives and mixtures thereof. The oil continuous benefit phase comprises a hydrocarbon based benefit material and a low HLB emulsifier. The hydrocarbon based benefit material is selected from petrolatum, mineral oil and mixtures thereof. The low HLB emulsifier comprises glycerol monooleate. The oil continuous benefit phase comprises a ratio of the hydrocarbon based benefit materials and a low HLB emulsifier comprises from about 30:1 to 200:1.

BRIEF DESCRIPTION OF THE DRAWINGS

FIG. 3 is a detailed cut away side view of one of the microplate holder of the automated cleansing unit, used in the in vitro deposition method.

DETAILED DESCRIPTION OF THE INVENTION

Figure 1:
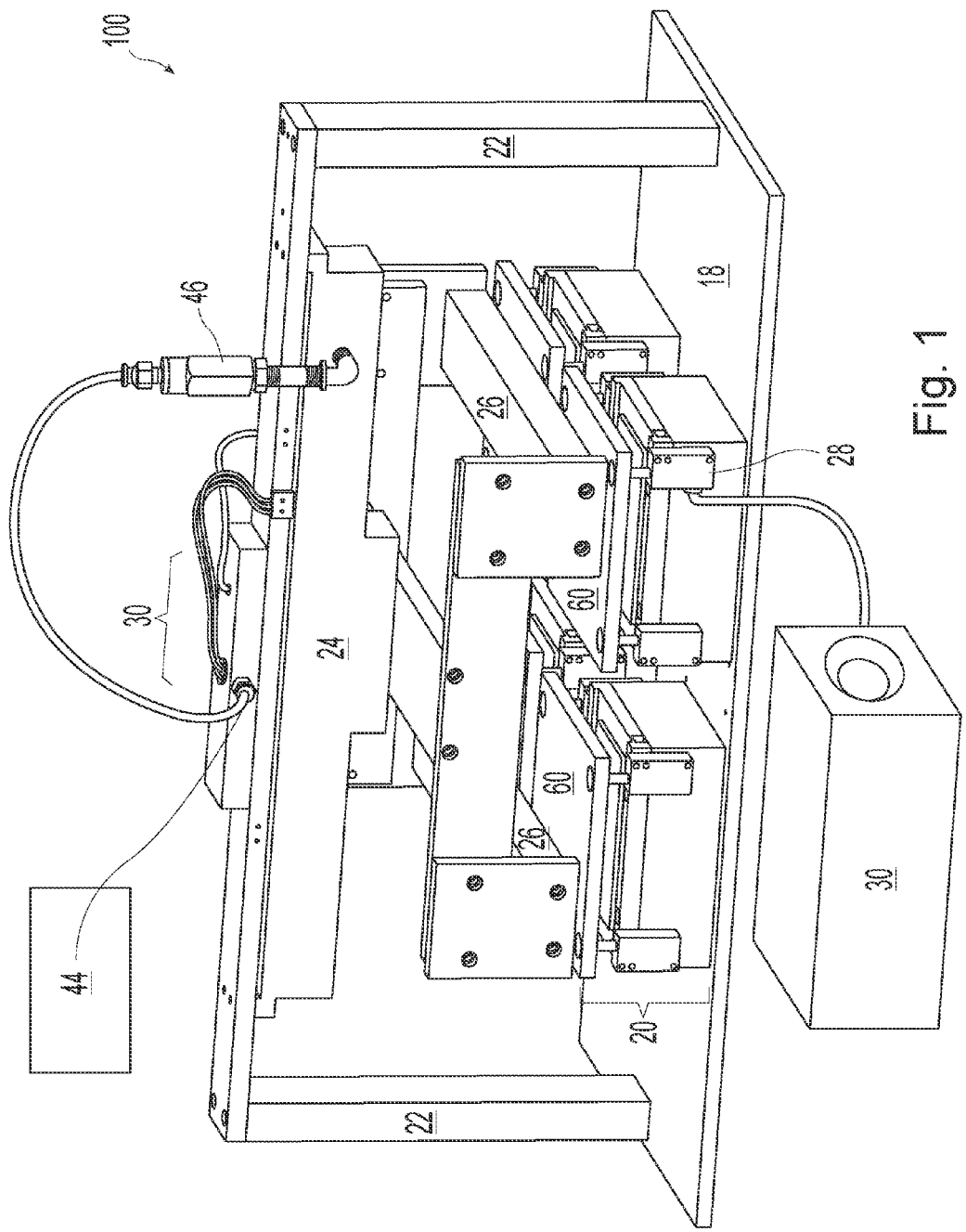
FIG. 1 is an isometric view of the automated cleansing unit used in the in vitro deposition method.

The term "anhydrous" as used herein, unless otherwise specified, refers to those phases, compositions and/or materials which are comprised, in some embodiments, of at less than about 3%, by weight, of water. In other embodiments, the phases, compositions, and/or materials comprise less than about 2%, by weight, of water and in other embodiments, less than about 1%, by weight, of water. The phases, compositions and/or materials which are comprised, in some embodiments, of zero %, by weight, of water.

The "coacervate," are used herein, refers to the chemical complex formed between cationic polymer and surfactants (e.g., anionic and amphoteric surfactants) upon dilution of the personal care composition. Coacervate formation is dependent upon a variety of criteria, such as molecular weight, component concentration, ratio of components, ionic strength of components, the charge density of the cationic components, charge density of the anionic components, the pH of the composition and the temperature of the composition. Coacervate systems and the effect of these parameters have been described, for example, in J. Caelles et al., *Anionic and Cationic Compounds in Mixed Systems*, 106 Cosmetics & Toiletries 49, 49-54 (April 1991), C. J. van Oss, *Coacervation, Complex-Coacervation and Flocculation*, 9 J. Dispersion Science and Tech., 561, 561-573, (1988-89), and in D. J. Burgess, *Practical Analysis of Complex Coacervate Systems*, 140 (1) J. of Colloid and Interface Science, 227, 227-238, (November 1990), all of which descriptions are incorporated herein by reference.

The term "HLB," as used herein is the balance between the hydrophilic and lipophilic moieties in a surfactant molecule and is used as a method of classification. HLB values for commonly-used surfactants are readily available in the literature, for example, in McCutcheon's Emulsifiers and Detergents North American Edition (MC Publishing Co. 1947) (2004). Another way of obtaining HLB values is to estimate by calculations. The HLB system was originally devised in by W. C. Griffin, *Calculation of "HLB" values of nonionic surfactants*, 1 J. Soc. Cosmetic Chemists, 311, 311-326 (1949). Griffin defined the HLB value of a surfactant as the mol % of the hydrophilic groups divided by 5, where a completely hydrophilic molecule (with no non-polar groups) had an HLB value of 20. Other examples of how to calculate HLB values are described by Davies et al. Interfacial Phenomena, 2nd Edition, (Academic Press, London 1963) and by I. J. Lin, *Hydrophile-lipophile balance (hlb) of fluorocarbon surfactants and its relation to the critical micelle concentration (cmc)* 76 (14) J. Phys. Chem. 2019, 2019-2013 (1972).

The term "multiphase" as used herein means that compositions comprise at least two phases which are chemically distinct (e.g. a surfactant phase and a benefit phase). These phases are in direct physical contact with one another and are not separated by a barrier. In some embodiments, the phases of the multiphase personal care composition are blended or mixed to a significant degree. In other embodiments, the phases of the multiphase personal care composition are made to occupy separate but distinct physical spaces inside the package in which they are stored, are not separated by a barrier and they are not emulsified or mixed to any significant degree. In one embodiment, the multi-phase personal care compositions comprise at least two visually distinct phases which are present within a container as a visually distinct pattern. The pattern results from the combination of the phases of the multiphase personal care composition by a method of manufacture herein described. The "patterns" or "patterned" include but are not limited to the following examples: striped, marbled, rectilinear, interrupted striped, check, mottled, veined, clustered, speckled, geometric, spotted, ribbons, helical, swirl, arrayed, variegated, textured, grooved, ridged, waved, sinusoidal, spiral, twisted, curved, cycle, streaks, striated, contoured, anisotropic, laced, weave or woven, basket weave, spotted, tessellated and mixtures thereof.

In one embodiment, the striped pattern can be relatively uniform across the dimension of the package. In another embodiment, the striped pattern is uneven (e.g. wavy), or non-uniform in dimension. The striped pattern does not extend across the entire dimension of the package in some embodiments. The stripe size is at least about 0.1 mm in width and 10 mm in length as measured from the exterior of the package in some embodiments. In another embodiment, the stripe size is about 1 mm in width and at least 20 mm in length as measured from the package exterior. In some embodiments, the phases are colored in order to offset its appearance from the other phase or phases present. In some embodiments, one phase contains particles, glitter or pearlescent agents in order to offset its appearance from the other phase or phases present.

The term "package" includes any suitable container for a personal care composition that exhibits a viscosity from about 1,500 centipoise (cP) to about 1,000,000 cP. The form of package includes in some embodiments bottles, tottles, tubes, jars, non-aerosol pumps and mixtures thereof.

The term "personal care composition" as used herein, refers to a composition that is formulated for topical application to the skin or hair. The personal care compositions are rinse-off personal care compositions that are formulated to be first applied topically to the skin and/or hair and subsequently rinsed off the skin and/or hair immediately, within minutes with water, or otherwise wiped off using a substrate or a device. In some embodiments, the personal care compositions are shaving creams that are formulated to be first applied topically to the skin for lubrication and subsequentially taken off with a shaving razor or rinsing with water during the act of shaving. The personal care composition is extrudable or dispensible from a package and, in most embodiments, exhibit a viscosity of from about 1,500 centipoise (cP) to about 1,000,000 cP. The form of the personal care compositions, some embodiments are liquid, semi-liquid, cream, lotion or gel. The form of the personal care composition, in some embodiments, can be solid or granular. In some embodiments, the personal care compositions include shampoo, conditioning shampoo, body wash, moisturizing body wash, shower gels, bar soaps, skin cleansers, cleansing milks, hair and body wash, in shower body moisturizer, pet shampoo, shaving creams and cleansing compositions used in conjunction with a disposable cleansing cloth.

The phrase "substantially free of" as used herein, unless otherwise specified, refers to those phases, compositions, or materials that comprise, in some embodiments, at less than about 3%; alternatively less than about 2%, and in some embodiments at less than about 0.1%, by weight, of a stated ingredient. Likewise, the term "free of" as used herein, refers to those phases, compositions, or materials that comprise, 0%, by weight, of a stated ingredient. Further, "free of" means that the stated ingredient has not been intentionally added to the composition, although the stated ingredient may incidentally form as a byproduct or a reaction product of other components of the phase, composition, or material.

The term "stable," as used herein, means that the multiphase personal care composition in some embodiments comprise less than 5% "third-phase" volume, less than 2% "third-phase" and less than 1% "third-phase" volume after undergoing the rapid protocol aging and third phase measurement, as described below in the "Third-Phase" Method.

The term "structured," as used herein means that the surfactant containing phase possesses a rheology that confers stability on the multiphase personal care composition. The structured surfactant phase is "structured," if the structured surfactant phase has one or more of the following properties described below:

A. The structured surfactant phase a Yield Stress, in most embodiments, of greater than about 0.1 Pascal (Pa), greater than about 0.5 Pa, greater than about 1.0 Pa, greater than about 2.0 Pa, greater than about 3 Pa, and greater than about 5 Pa, as measured by the Yield Stress and Zero Shear Viscosity Method described hereafter:

B. The structured surfactant phase has a Zero Shear Viscosity, in most embodiments, of at least about 500 Pascal-seconds (Pa-s), at least about 1,000 Pa-s, at least about 1,500 Pa-s, and at least about 2,000 Pa-s;

C. The structured surfactant phase has a Structured Domain Volume Ratio, in most embodiments, of greater than about 40%, at least about 45%, at least about 50%, at least about 55%, at least about 60%, at least about 65%, at least about 70%, at least about 75%, at least about 80%, at least about 85% by the Ultracentrifugation Method described hereafter, and/or D. The structured surfactant phase has a Young's Modulus, in most embodiments, of greater than about 10 Pascal (Pa), greater than about 50 Pa, greater than about 75 Pa, and greater than about 100 Pa.

The term "surfactant component" as used herein, means the total of all anionic, nonionic, amphoteric, zwitterionic and cationic surfactants in a phase. It follows that when calculations are based on the "surfactant component," both water and electrolyte are excluded from the calculations since surfactants are typically diluted and neutralized when manufactured.

As used herein "tottle" refers to a bottle that has as its base on its neck or mouth, through which its contents are filled and dispensed from. This base is also the end upon which the bottle is intended to rest or sit upon for storage by the consumer and/or for display on the store shelf. Typically, the closure on a tottle is flat or concave, such that, when the tottle is stored or displayed it rests on the closure. Suitable tottles are described in the Multi-phase Personal Care Compositions, Process for Making and Providing An Article of Commerce, U.S. patent application Ser. No. 11/067,443 (filed on Feb. 25, 2005).

The term "visually distinct" as used herein, refers to the difference regions of the multiphase personal care composition which are visible to the unaided naked eye. For example, one region having a first average composition, as compared to a second region having a second average composition, wherein the difference between the first region and the second region are visible to the unaided naked eye. This would not preclude the distinct regions in some embodiments, from comprising two similar phases wherein one phase comprises pigments, dyes, particles and/or various optional ingredients, making the a region have a different average composition. In most embodiments, a phase occupies a space having dimensions larger than the colloidal or sub-colloidal components it comprises. In most embodiments, a phase has the ability to be constituted, re-constituted, collected, or separated into a phase in order to observe its properties, for example, by centrifugation, filtration or the like.

The exemplified multiphase personal care compositions of the present invention show a significant increase in deposition of hydrocarbon based materials relative to the comparative examples below. Without wishing to be bound by theory, it is believed that the synergistic combination of the cationic deposition polymer and the ratio of the hydrocarbon based benefit materials to low HLB emulsifiers in multiphase personal care compositions of the present invention which enhance coacervate formation. The increased coacervate formation results in the increased deposition of hydrocarbon based materials by the exemplified multiphase personal care composition of the present invention.

Structured Surfactant Phase

The multiphase personal care composition comprises a structured surfactant phase. In some embodiments, the multiphase personal care composition from about 10% to about 22%, by weight of a multiphase personal care composition, of a structured surfactant phase. The multiphase personal care composition comprises from about 15% to about 22%, by weight of a multiphase personal care composition, of a structured surfactant phase. The structured surfactant phase is comprised of a structured domain that comprises a mixture of lathering surfactants. In some embodiments, the structured domain is an opaque structured domain. The opaque structured domain, in some embodiments, is a lamellar phase. The lamellar phase produces a lamellar gel network. In some embodiments, the lamellar phase is resistant to shear, has adequate yield to suspend particles and droplets, and provides long term stability. Lamellar phases, in most embodiments, are thermodynamically stable. In most embodiments, the lamellar phase possesses a viscosity that minimizes the need for the addition of viscosity modifiers.

The structured surfactant phase, in some embodiments, comprises a mixture of surfactants. The multiphase personal care composition, in some embodiments, comprises from about 5% to about 30%, by weight of the multiphase personal care composition, of a mixture of lathering surfactants. In other embodiments, the multiphase personal care composition comprises from about 15% to about 22%, by weight of the multiphase personal care composition, of a mixture of lathering surfactants. The mixture of lathering surfactants is compatible with other components of the multiphase personal care composition including water. The mixture of lathering surfactants, in some embodiments, is selected from anionic, nonionic, cationic, zwitterionic, amphoteric surfactants, soap and mixtures thereof. In some embodiments, the mixture of lathering surfactants is selected from anionic surfactants, amphoteric surfactants, nonionic surfactants and mixtures thereof due to the coacervate formation ability of these selected surfactants with cationic deposition polymers. Suitable surfactants for the multiphase personal care composition are described in McCutcheon's: Detergents and Emulsifiers North American Edition (Allured Publishing Corporation 1947) (1986), McCutcheon's, Functional Materials North American Edition (Allured Publishing Corporation 1973) (1992) and U.S. Pat. No. 3,929,678 (filed Aug. 1, 1974).

The structured surfactant phase, in some embodiments, comprises from about 10% to about 20%, by weight of the structured surfactant phase, of anionic surfactants. The anionic surfactants are selected from linear anionic surfactants, branched anionic surfactants and mixtures thereof. Suitable linear anionic surfactants are selected from ammonium lauryl sulfate, ammonium laureth sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, potassium lauryl sulfate, and mixtures thereof. The multiphase personal care composition comprises at least one branched anioinic surfactants, in some embodiments. Suitable branched anionic surfactants are selected from sodium trideceth sulfate, sodium tridecyl sulfate, sodium $C_{12-13}$ alkyl sulfate, $C_{12-13}$ pareth sulfate, sodium $C_{12-13}$ pareth-n sulfate, monomethyl branched anionic surfactants and mixtures thereof. Other suitable branched anionic surfactants include those described in Stable, Patterned Multi-Phased Personal Care Composition, U.S. patent Publication Ser. No. 11/197,866 (filed Aug. 5, 2005) (published on Apr. 13, 2006).

The structured surfactant phase comprises from about 3% to about 6%, by weight of the structured surfactant phase, of amphoteric surfactant. Suitable amphoteric surfactant include those that are broadly described as derivatives of aliphatic secondary and tertiary amines in which the aliphatic radical can be straight or branched chain and wherein one of the aliphatic substituents contains from about 8 to about 18 carbon atoms and one of the aliphatic substituents contains an anionic water solubilizing group, such as a carboxy, a sulfonate, a sulfate, a phosphate, or a phosphonate. Examples of suitable amphoteric surfactants are selected from sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072 (filed May 17, 1951), N-higher alkyl aspartic acids such as those produced according to the teaching of U.S. Pat. No. 2,438,091 (filed Sep. 6, 1943), and the products described in U.S. Pat. No. 2,528,378 (filed Sep. 20, 1947). The multiphase personal care composition, in some embodiments, comprises an amphoteric surfactant selected from the group of sodium lauroamphoacetate, sodium cocoamphoactetate, disodium lauroamphoacetate disodium cocodiamphoacetate and mixtures thereof. Amphoacetates and diamphoacetates can be used in the multiphase personal care composition in some embodiments.

The structured surfactant phase, in some embodiments, comprises zwitterionic surfactants. Suitable zwitterionic surfactants include those described as derivatives of aliphatic quaternary ammonium, phosphonium, and sulfonium compounds, in which the aliphatic radicals can be straight or branched chain, and wherein one of the aliphatic substituents comprise from about 8 to about 18 carbons and one of the aliphatic substituents contains an anionic water solubilizing group, such as a carboxy, a sulfonate, a sulfate, a phosphate, or a phosphonate. In other embodiments, suitable zwitterionic surfactants comprise betaines selected from coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl)carboxymethyl betaine, oleyl dimethyl gamma-carboxypropyl betaine, lauryl bis-(2-hydro-xypropyl)alpha-carboxyethyl betaine, coco dimethyl sulfopropyl betaine, stearyl dimethyl sulfopropyl betaine, amido betaines, amidosulfobetaines and mixtures thereof.

Suitable cationic surfactants, in some embodiments, are selected from stearyldimenthylbenzyl ammonium chloride, dodecyltrimethylammonium chloride, nonylbenzylethyldimethyl ammonium nitrate, tetradecylpyridinium bromide, laurylpyridinium chloride, cetylpyridinium chloride, laurylpyridinium chloride, laurylisoquinolium bromide, ditallow (hydrogenated) dimethyl ammonium chloride, dilauryldimethyl ammonium chloride, stearalkonium chloride, and mixtures thereof.

The structured surfactant phase, in some embodiments, comprise from about to 1% about 3%, by weight of the structured surfactant phase, of a nonionic surfactant. Suitable nonionic surfactants include glucose amides, alkyl polyglucosides, sucrose cocoate, sucrose laurate, alkanolamides, ethoxylated alcohols and mixtures thereof in some embodiments. Other suitable nonionic surfactants include glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

Lamellar Phase Inducing Agent

The structured surfactant phase comprises a lamellar phase inducing agent. In some embodiments, the structured surfactant phase comprises from about 0.3% to about 15%, by weight of the structured surfactant phase, of lamellar phase inducing agent. The structured surfactant phase, in some embodiments, comprises from about 0.5% to about 5% by weight of the structured surfactant phase, of lamellar phase inducing agent. Not being bound by theory, the lamellar phase inducing agent functions in the multiphase personal care compositions to form a thermodynamic domain and in most embodiments, form lamellar domain. It is believed the lamellar domain enhances the interfacial stability between the structured surfactant phase and the oil continuous benefit phase of the multiphase personal care composition of the present invention. Suitable lamellar phase inducing agents include electrolyte, non-ionic surfactant, fatty acids, ester derivatives, fatty alcohols, trihydroxystearin (available from Rheox, Inc. under the trade name THIXCIN® R) in some embodiments.

The structured surfactant phase, in some embodiments, comprise from about 0.1% to about 6%, by weight of the structured surfactant phase, of electrolyte. In other embodiment, the structured surfactant phase comprises from about 1% to about 5% and from about 2% to about 5%, by weight of structured surfactant phase, of electrolyte. The structured surfactant phase, in some embodiments, comprise from about 3% to about 6%, by weight of the structured surfactant phase, of electrolyte. The electrolyte is added per se into the structured surfactant phase in some embodiments. In other embodiments, the electrolyte is formed in situ via the counterions included in one or more raw materials. Electrolytes are formed from an anion and a cation. Suitable anions, in some embodiments, comprise phosphate, chloride, sulfate and citrate. Suitable cations, in come embodiments, comprise sodium, potassium, magnesium and mixtures thereof. In some embodiments, suitable electrolytes comprise sodium chloride, ammonium chloride, sodium sulfate an ammonium sulfate.

Suitable nonionic surfactants which act as lamellar phase inducing agents, in some embodiments, comprise isosteareth-2, laureth-2, and trideceth-3. Suitable fatty acids which act as lamellar phase inducing agents, in some embodiments include fatty acids having carbon chain lengths of $C_{10}$-$C_{22}$, such as, lauric acid, oleic acid, isostearic acid, linoleic acid, linolenic acid, ricinoleic acid, elaidic acid, arichidonic acid, myristoleic acid and palmitoleic acid, and the like. Suitable ester derivatives which act as lamellar phase inducing agents, in some embodiments include propylene glycol isostearate, propylene glycol oleate, glyceryl isostearate, glyceryl oleate, propylene glycol dilaurate, polyglyceryl diisostearate, lauryl behenate and the like. In some embodiments, the lamellar phase inducing agents are selected from lauric acid, trihydroxystearin, lauryl pyrrolidone, and tridecanol.

Cationic Deposition Polymer

The structured surfactant phase comprises a cationic deposition polymer. In some embodiments, the structured surfactant phase comprises from about 0.1% to about 5%, by weight of the structured surfactant phase, of cationic deposition polymer. The structured surfactant phase comprises from about 0.5% to about 1%, by weight of the structured surfactant phase, of cationic deposition polymer. It believed that the cationic deposition polymers provide the desirable silky, soft, smooth in-use feeling to the multiphase personal care composition of the present invention. Not to bound by theory, it is believed that the presence of cationic deposition polymer within the structured surfactant phase assists in providing increased deposition of the benefit agents in combination with the oil continuous benefit phase. Further, it is believed that the amount and type of cationic deposition polymer used in the structured surfactant phase effects both formation of coacervates and deposition of benefit agents. If a large amount of cationic deposition polymers is added, the resultant personal care composition possesses a suppressed lather volume and negative in-use characteristics. Conversely, if only a small amount of cationic deposition polymer is added, the resultant personal care composition does not form coacervates and does not deposit benefit agents. Most embodiments, of the cationic deposition polymer comprises the selection of a cationic guar, a cationic guar derivative and mixtures thereof due to the selections significant synergy with the oil continuous benefit phase. The general structure of cationic guar and cationic guar derivatives are shown below:

3215, N-Hance 3269, N-Hance 3270). The cationic guar gum polymers in the present invention have been found to be more effective for enhancing oil continuous benefit phase deposition than those cationic polymers based on hydroxyethyl cellulose (e.g., JR-30M, KG-30M, JR400 commercially available from Dow Chemical) and hydropropyl guar hydroxypropyltrimonium chloride (e.g., Jaguar C162 from Rhodia).

Polymeric Phase Strucurant

The structured surfactant phase, in some embodiments, comprises from about 0.05% to about 5%, by weight of the multiphase personal care composition, of one or more poly-

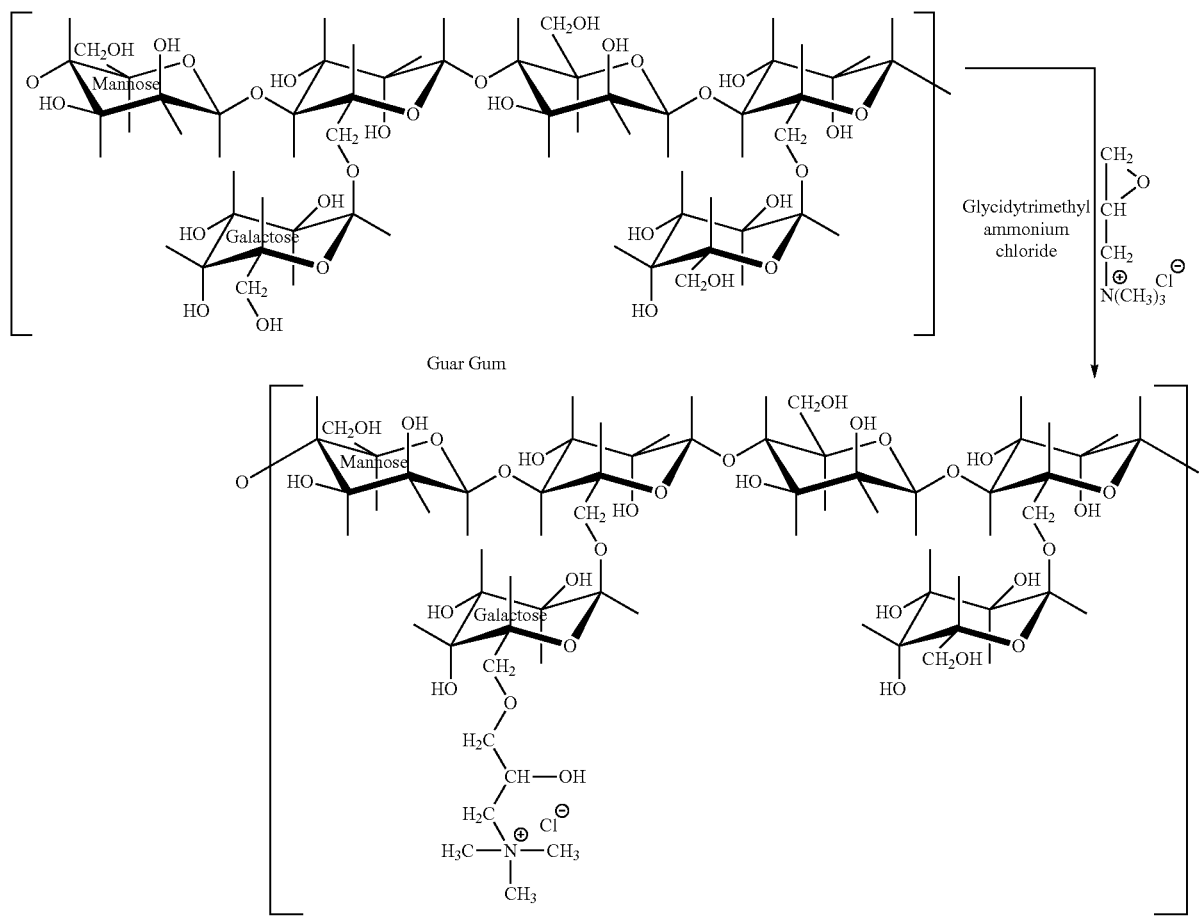

Guar Hydroxyprpyltrimonium Chloride (CAS 65497-29-2)(DS$_{quat}$ = # quat groups/sugar unit In some embodiments, the average molecular weight of the cationic guar is between 5,000 to about 10 million. In other embodiments, the average molecular weight of the cationic guars is at least about 100,000, is at least about 200,000, and is at least about 500,000. In some embodiments, the cationic guar comprises a charge density ranging from about 0.2 meq/gm to about 5 meq/gm. In other embodiments, the cationic guar comprises a charge density ranging from at least about 0.4 meq/gm, more preferably at least about 0.6 meq/gm. Examples of commercial available cationic guars include JAGUAR® from Rhodia (Jaguar C13S, Jaguar C14S, Jaguar C-17, Hi-Care 1000, Jaguar Excel, Jaguar CHT), and N-HANCE® polymers from Aqualon (N-Hance 3000, N-Hance 3196, N-Hance 3198, N-Hance 3205, N-Hance meric phase structurants. In other embodiments, the structured surfactant phase, in some embodiments, comprises from about 0.1% to about 3%, by weight of the multiphase personal care composition, of one or more polymeric phase structurants. Suitable polymeric phase structurants, in some embodiments, include naturally derived polymers, synthetic polymers, crosslinked polymers, block copolymers, copolymers, hydrophilic polymers, nonionic polymers, anionic polymers, hydrophobic polymers, hydrophobically modified polymers, associative polymers, and oligomers. Suitable associative polymers, in some embodiments, include hydrophobically modified polyacrylates, hydrophobically modified polysaccharides and hydrophobically modified urethanes. Other embodiments of suitable associative polymers include acrylates/vinyl isodecanoate crosspolymer (e.g. STABYLEN 30® from 3V), acrylates/C10-30 alkyl acrylate crosspolymer (e.g. PEMULEN TR10 and PEMULEN TR2), ammonium acryloyldimethyltaurate/beheneth-25 methacrylate crosspolymer (e.g. ARISTOFLEX® HMB from Clariant), arylates/beheneth-25 methacrylate copolymer (e.g. ACULYN® 28 from Rohm and Haas), acrylates/steareth-20 methacrylate copolymer (e.g. ACULYN® 22 from Rohm and Haas), PEG-150/decyl alcohol/SMDI copolymer (e.g. ACULYN® 44 from Rohm and Haas), PEG-150 distearate (e.g. ACULYN® 60 from Rohm and Haas), acylates/steareth-20 methacrylate crosspolymer (e.g. ACULYN® 88 from Rohm and Haas).

Oil Continuous Benefit Phase

The multiphase personal care composition, in some embodiments, comprises from about 10% to about 50%, by weight of the multiphase personal care composition, of a oil continuous benefit phase. In most embodiments, the oil continuous benefit phase is anhydrous. The oil continuous benefit phase, in other embodiments, is substantially free of water or free of water. The oil continuous benefit phase is substantially free or free of a lathering surfactant, in some embodiments. The oil continuous benefit phase comprises a hydrocarbon based benefit material and a low HLB emulsifier comprising unsaturated monoglyceryl ester having from about 14 to about 30 carbon atoms.

The oil continuous benefit phase comprises a ratio of hydrocarbon based benefit material and a low HLB emulsifier. The ratio of hydrocarbon based benefit material and a low HLB emulsifier ranges from about 30:1 to about 200:1. The multiphase personal care composition, in some embodiments, comprises a ratio of hydrocarbon based benefit materials to the low HLB emulsifier which is 95:1. In other embodiments, the multiphase personal care composition comprises a ratio of hydrocarbon based benefit materials to the low HLB emulsifier which is 80:1. The multiphase personal care composition, in some embodiments, comprises a ratio of hydrocarbon based benefit materials to the low HLB emulsifier which is 49:1. It is believed that this ratio allows enhanced deposition of the hydrocarbon based benefit material without negatively impacting lather performance.

Hydrocarbon Benefit Material

The oil continuous benefit phase, in some embodiments, comprises from about 10% to about 99%, by weight of the multiphase personal care composition, of a hydrocarbon based benefit material. In other embodiments, oil continuous benefit phase comprises from about 30% to about 99%, by weight of the multiphase personal care composition, of a hydrocarbon based benefit material. The oil continuous benefit phase comprises from about 50% to about 99%, by weight of the multiphase personal care composition, of a hydrocarbon based benefit material. In some embodiments, the multiphase personal care composition comprises a ratio of structured surfactant phase to oil continuous benefit phase, of from about 2:1 to about 1:5.

Hydrocarbon based benefit materials suitable in the present invention have a Young's Modulus between 100 to 2,000 Pa. In some embodiments, the hydrocarbon based benefit material comprises greater than about 20 carbon atoms. The hydrocarbon based benefit material, in other embodiments, comprises greater than about 30 carbon atoms. In other embodiments, the hydrocarbon based material comprises greater than about 40 carbon atoms.

The hydrocarbon based benefit materials for use in the oil continuous benefit phase of the multiphase personal care composition have a preferred rheology profile, as defined by consistency value (k) and shear index (n) are described in the Test Methods below. The hydrocarbon based benefit materials for use in the oil continuous benefit phase have a consistency value, in some embodiments of ranging from about 1 to about 10,000 poise (1/sec).$^{n-1}$ In other embodiments, the hydrocarbon based benefit materials have a consistency value in the range of about 10 to about 2000 poise (1/sec).$^{n-1}$ The hydrocarbon based benefit materials have a consistency value in the range of about 50 to about 1000 poise (1/sec)$^{n-1}$ in other embodiments. The hydrocarbon based benefit materials for use in the oil continuous benefit phase have a shear index, in some embodiments; range from about 0.1 to about 0.8. In other embodiments, the hydrocarbon based benefit materials have a shear index value in the range of from about 0.1 to about 0.5. The hydrocarbon based benefit materials have a shear index in the range of from about 0.20 to about 0.4. These rheological properties are useful in providing a multiphase personal care composition that has improved deposition of hydrocarbon based benefit materials onto the skin.

The oil continuous benefit phase, in some embodiments, comprises hydrocarbon based benefit materials selected from petrolatum, hydrocarbon oils (e.g. mineral oil), natural and synthetic waxes (e.g. micro-crystalline waxes, paraffins, ozokerite, polyethylene, polybutene, polydecene, pentahydrosqualene) and mixtures thereof. In one embodiments, at least about 50% by weight of the hydrophobic benefit materials are selected from petrolatum, mineral oil, paraffins, polyethylene, polybutene, polydecene, and versagel. The oil continuous benefit phase, in some embodiments, is comprised of a combination of petrolatum and mineral oil.

Low HLB Emulsifier

The oil continuous benefit phase comprises from about 0.1% to about 4%, by weight of the multiphase personal care composition, of a low HLB emulsifier. In other embodiments, the oil continuous benefit phase comprises from about 0.25% to about 3%, by weight of the multiphase personal care composition, of a low HLB emulsifier. The oil continuous phase, in some embodiments, comprises from about 0.5% to about 3%, by weight of the multiphase personal care composition, of a low HLB emulsifier. In other embodiments, the oil continuous benefit phase, comprises from about 1.0% to about 3%, by weight of the multiphase personal care composition, of a low HLB emulsifier. The oil continuous benefit phase comprises, in other embodiments, comprises from about 1.5% to about 2.5%, by weight of the multiphase personal care composition, of a low HLB emulsifier.

The oil continuous benefit phase comprises a low HLB emulsifier comprising unsaturated monoglyceryl ester having from about 14 to about 30 carbon atoms. In one embodiment, the unsaturated monoglyceryl ester having from about 14 to about 30 carbon atoms is glycerol monooleate. One suitable embodiment of glycerol monooleate is manufactured under the tradename GMO supplied from Cognis that has a HLB of 3.8. In another embodiment, the unsaturated monoglyceryl ester having from about 14 to about 30 carbon atoms is glyceryl linoleate which is a monoester of glycerin and linoleic acid. In another embodiment, the unsaturated monoglyceryl ester having from about 14 to about 30 carbon atoms is glyceryl linolenate which is a monoester of glycerin and linolenic acid.

In some embodiments, the low HLB emulsifier comprises an additional low HLB emulsifier. The low HLB emulsifier comprises a HLB from about 1.5 to 10, in some embodiments. In other embodiments, the low HLB emulsifier comprises an HLB of from about 3 to 10. In other embodiments, the low HLB emulsifier comprises a HLB of from about 3 to about 8. The low HLB emulsifier comprises a HLB of from about 3 to about 6, in some embodiments.

Suitable low HLB emulsifiers include, in some embodiments, are those selected from glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, silicone copolyols and mixtures thereof. Suitable silicone copolyols, in some embodiments, include ABIL EM-90® from Evonik, KF-6038 from Shin Etsu, DC5200 and DC5225 from Dow Corning.

Some embodiments of suitable low HLB emulsifiers are listed in the table below:

TABLE 1

Examples of low HLB emulsifiers

| Chemical Name | Supplier | HLB |
| --- | --- | --- |
| Sorbitan Monooleate | SPAN ® 80 from Uniqema | 4.3 |
| Sorbitan Stearate (and) Sucrose Cocoate | ARLATONE ® 2121 from Uniqema | 6 |
| Trideceth-3 | LUTENSOL ® TDA-3 from BASF | 8 |
| Polyglyceryl-2 Triisostearate | PRISORINE ® 3793 from Uniqema | 2.5 |
| Sorbitan Stearate | HETAN SS from 7 World | 4.7 |
| Polyhydroxystearate | ISOLAN ® gps from Degussa | 5 |
| Polyglyceryl-3 Diisostearate | LAMEFORM ® TGI from Degussa | 6 |
| 66.7% polyglycerine 66.7/ 33.33% poly(12-hydroxystearic acid) | DEHYMULS ® PGPH from Cognis | 5 |
| Steareth-2 | BRIJ ® 72 from Uniqema | 5 |
| Ceteth-2 | BRIJ ® 52 from Uniqema | 5.3 |
| Propylene Glycol Isostearate | PRISORINE ® 2034 from Uniqema | 1.5 |

Benefit Phase Structurant

The oil continuous benefit phase, in some embodiments, comprises less than 75%, by weight of the oil continuous benefit phase, of a benefit phase structurant. In other embodiments, the oil continuous benefit phase comprises less than 50%, of the oil continuous benefit phase, of benefit phase structurant. The oil continuous benefit phase, in other embodiments, comprises less than 35%, by weight of the oil continuous benefit phase, of benefit phase structurant. The benefit phase structurant, in some embodiments, functions to correct the rheological properties of the oil continuous benefit phase and assists in providing effective deposition and retention of hydrocarbon based benefit materials on the skin. The oil continuous benefit phase has a viscosity in the range of from about 100 to about 200,000 poise. In some embodiments, oil continuous benefit phase has a viscosity in the range of from about 200 to about 100,000 poise. In other embodiments, oil continuous benefit phase has a viscosity in the range of from about 200 to about 50,000 poise. The amount of benefit phase structurant required to produce the targeted viscosity range will vary and is dependant on the hydrocarbon based benefit materials in the oil continuous benefit phase and those in the benefit phase structurant.

Suitable benefit phase structurants, in some embodiments, comprise solid fatty acid esters, natural fats, modified fats, fatty acids, fatty amines, fatty alcohols, natural waxes, synthetic waxes, petrolatum, block copolymers (e.g. KRATON® by Shell), hydrophobically modified silica, hydrophobically modified clay (e.g. BENTONE 27V, BENTONE 38V or BENTONE GEL MIOV from Rheox and CAB-O-SIL TS720 or CAB-O-SIL M5 from Cabot Corporation) and mixtures thereof. Structurants meeting the above requirements in combination with the hydrocarbon based benefit material in the oil continuous benefit phase form a three dimensional networks to build up the viscosity of the hydrocarbon based benefit material. It is believed that these three dimensional networks provide both in-use and after-use benefits due to their shear thinning rheological properties and the weak structure of the network.

In some embodiments, the personal care compositions comprises from about 0.001% to less than about 6%, less than about 5%, less than about 4%, less than about 3%, less than about 2%, less than about 1%, less than about 0.5%, less than about 0.25%, less than about 0.1%, less than about 0.01%, less than about 0.005%, by weight of the personal care composition, of one or more optional ingredients selected from thickening agents, preservatives, antimicrobials, fragrances, chelators, such as those described in U.S. Pat. No. 5,487,884 (filed Oct. 22, 1982), sequestrants, density modifiers (e.g. low density modifiers comprising gas filled microspheres under the trade name EXPANDCEL® available from Akzo Nobel), vitamins (e.g. Retinol), vitamin derivatives (e.g. tocophenyl actetate, niacinamide, panthenol), sunscreens, desquamation actives, such as those described in U.S. Pat. No. 5,681,852 (filed Jun. 7, 1995) and U.S. Pat. No. 5,652,228 (filed Nov. 12, 1993), anti-wrinkle/anti-atrophy actives (e.g. N-acetyl derivatives, thiols, hydroxyl acids, phenol), anti-oxidants (e.g. ascorbic acid derivatives, tocophenol), skin soothing agents/skin healing agents (e.g. panthenoic acid derivatives, aloe vera, allantoin), skin lightening agents (e.g. kojic acid, arbutin, ascorbic acid derivatives), skin tanning agents (e.g. dihydroxyacteone), anti-acne medicaments; essential oils, sensates; pigments; colorants; pearlescent agents; interference pigments, such as those disclosed in U.S. Pat. No. 6,395,691 (filed Feb. 28, 2001), U.S. Pat. No. 6,645,511 (filed Jan. 16, 2002), U.S. Pat. No. 6,759,376 (filed Sep. 11, 2002) and U.S. Pat. No. 6,780,826 (filed Sep. 11, 2002) particles (e.g. talc, kolin, mica, smectite clay, cellulose powder, polysiloxane, silicas, carbonates, titanium dioxide, polyethylene beads), hydrophobically modified non-platelet particles described in Personal Care Compositions Containing Hydrophobically Modified Non-platelet particle, U.S. Patent Pub. No. 2006/0182699A (filed Feb. 15, 2005) (published on Aug. 17, 2006) and mixtures thereof. Such optional ingredients are most typically those materials approved for use in cosmetics and that are described in reference books such as the CTFA Cosmetic Ingredient Handbook, Second Edition (The Cosmetic, Toiletries, and Fragrance Association, Inc. 1988)(1992).

Method of Use

The multiphase personal care compositions of the present invention are applied topically to the desired area of the skin or hair in an amount sufficient to effectively deliver surfactants, hydrocarbon based benefit material, and/or optional materials to the desired area of the skin and hair. In some embodiments, the multiphase personal care composition is applied directly to the desired area of skin or hair. In other embodiments, the multiphase personal care composition is applied via the use of a cleansing puff, washcloth, sponge or other implement. In some embodiments, the multiphase personal care compositions are used as shaving aids, which are formulated to be first applied topically to the skin for lubrication and subsequentially taken off with a shaving razor or rinsing with water during the act of shaving. The multiphase personal care composition, in most embodiments, is diluted with water prior to, during, or after topical application. After application, the multiphase personal care composition is subsequently rinsed or wiped off the skin or hair within minutes using water or a water-insoluble substrate in combination with water.

Method of Manufacture

In one embodiment, the personal care articles of the present invention are manufactured by a dual phase filler. The dual phase filler is associated with storage vessels, a combiner, a blender and nozzle for filling the phases of multiphase personal care composition. An example of a dual phase filler and associated software is manufactured by Antonio Mengibar Packaging Machinery of Barcelona, Spain. The structured surfactant phase and oil continuous benefit phase of the multiphase personal care compositions are stored in separate storage vessel; each vessel equipped with a pump and a hose assembly. A programmed filler profile of the dual-phase filler controls the pumping of specific ratios of the two phases of the multiphase personal care composition. The two phases of the personal care compositions are pumped from the storage tanks into a combiner where the two phases are combined. After the phases are combined; they are mixed in a blender. From the blender, the resultant product is pumped via a hose into a single nozzle. The nozzle is placed into a container and fills a product package with a single resulting product. In some embodiments, the resultant product exhibits a distinct pattern of the phases which are visually distinct. In other embodiments, the resultant product exhibits a uniform appearance without a pattern. If a pattern is present, the pattern is selected from the group consisting of striped, marbled, geometric, and mixtures thereof.

In another embodiment, the personal care compositions of the present invention are manufactured according to the method disclosed in Visually distinctive multiple liquid phase compositions, U.S. Patent Application Pub. No. 2004/0219119 (filed Apr. 30, 2004) (published Nov. 18, 2004). Alternatively, it may be effective to combine toothpaste-tube filling technology with a spinning stage design. In still another embodiment, the personal care compositions are prepared by the method and apparatus as disclosed in U.S. Pat. No. 6,213,166 (filed Jan. 12, 2000). The method and apparatus allows two or more compositions to be filled with a spiral configuration into a single product package. The method requires that at least two nozzles be employed to fill the compositions into a package. The package is placed on a moving stage and spun as the composition is introduced into the package.

Test Methods

Ultracentrifugation Method:
The Ultracentrifugation Method is used to determine the percent of a structured domain or an opaque structured domain that is present in a multiphase personal care composition that comprises a surfactant phase or a surfactant component. The method involves the separation of a multiphase personal care composition by ultracentrifugation into separate but distinguishable layers. The multiphase personal care composition comprises multiple distinguishable layers, for example a non-structured surfactant layer, a structured surfactant layer, and a benefit layer.

First, about 4 grams of sample of the multiphase personal care composition are dispensed into centrifuge tubes, such as a Beckman Coulter centrifuge tube that is 11 mm by 60 mm. Next, centrifuge tubes are placed into a ultracentrifuge, such as Ultracentrifuge OPTIMA™ L-80 (Beckman Instruments, Inc., Fullerton, Calif.). The samples are centrifuged at 50,000 rpm at 25° C. for 18 hours. After ultracentrifugation, the relative phase volume is determined by measuring the height of each layer visually using an Electronic Digital Caliper (within 0.01 mm).

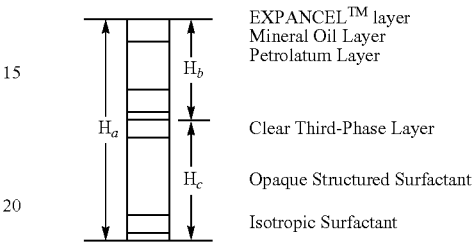

First, the total height is measured as $H_a$ which includes all materials in the ultracentrifuge tube. Second, the height of the benefit layer is measured as $H_b$. Third, the structured surfactant layer is measured as H. The benefit layer is determined by its low moisture content (e.g. less than 10% water as measured by Karl Fischer Titration). It generally presents at the top of the centrifuge tube.

The total surfactant layer height ($H_s$) can be calculated by this equation:

$$H_s = H_a - H_b$$

The structured surfactant layer $H_c$, in some embodiments, comprises one layer. In other embodiments, the structured surfactant layer $H_c$, the structured surfactant layer, comprises several layers. In such as case, the structured surfactant layer $H_c$, comprises the sum of the individual structure layers. In some embodiments, upon ultracentrifugation, there is generally an isotropic layer at the bottom or next to the bottom of the ultracentrifuge tube which represents the non-structured micellar surfactant layer. The layers above the isotropic phase generally comprise higher surfactant concentration with higher ordered structures (i.e. such as liquid crystals). These structured layers are sometimes opaque to naked eyes, or translucent, or clear. There is generally a distinct phase boundary between the structured layer and the non-structured isotropic layer. The physical nature of the structured surfactant layers can be determined through microscopy under polarized light. The structured surfactant layers typically exhibit distinctive texture under polarized light. Another method for characterizing the structured surfactant layer is to use X-ray diffraction technique. Structured surfactant layer display multiple lines that are often associated primarily with the long spacings of the liquid crystal structure. If a coacervate phase or any type of polymer-surfactant phase is present, it is considered a structured phase.

Finally, the structured domain volume ratio is calculated as follows:

$$\text{Structured Domain Volume Ratio} = H_c/H_s * 100\%$$

If there is no benefit phase present, use the total height as the surfactant layer height, $H_s = H_a$.

Yield Stress, Young's Modulus and Zero Shear Viscosity Method:
The Yield Stress and Zero Shear Viscosity of a multiphase personal care composition, in some embodiments, can be measured prior to combining the phases of the composition. In other embodiments, the Yield Stress and Zero Shear Viscosity, can be measured after combining the phases in a composition wherein the phases of the multiphase personal care composition would first be separates by any suitable physical separation means, such as centrifugation, pipetting, cutting away mechanically, rinsing, filtering, or other separation means. A controlled stress rheometer, such as a TA Instruments AR2000 Rheometer, is used to determine the Yield Stress and Zero Shear Viscosity. The determination is performed at 25° C. with the 4 cm diameter parallel plate measuring system and a 1 mm gap. The geometry has a shear stress factor of 79580 $m^{-3}$ to convert torque obtained to stress. Serrated plates can be used to obtain consistent results when slip occurs.

First a sample of the phase is obtained and placed in position on the rheometer base plate, the measurement geometry (upper plate) moving into position 1 mm above the base plate. Excess phase at the geometry edge is removed by scraping after locking the geometry. If the phase comprises particles discernible to the eye or by feel (beads, e.g.) which are larger than about 150 microns in number average diameter, the gap setting between the base plate and upper plate is increased to the smaller of 4 mm or 8-fold the diameter of the $95^{th}$ volume percentile particle diameter. If a phase has any particle larger than 5 mm in any dimension, the particles are removed prior to the measurement.

The determination is performed via the programmed application of a continuous shear stress ramp from 0.1 Pa to 1,000 Pa over a time interval of 4 minutes using a logarithmic progression, i.e., measurement points evenly spaced on a logarithmic scale. Thirty (30) measurement points per decade of stress increase are obtained. Stress, strain and viscosity are recorded. If the measurement result is incomplete, for example if material flows from the gap, results obtained are evaluated and incomplete data points excluded. The Yield Stress is determined as follows. Stress (Pa) and strain (unitless) data are transformed by taking their logarithms (base 10). Log(stress) is graphed vs. log(strain) for only the data obtained between a stress of 0.2 Pa and 2.0 Pa, about 30 points. If the viscosity at a stress of 1 Pa is less than 500 Pa-sec but greater than 75 Pa-sec, then log(stress) is graphed vs. log(strain) for only the data between 0.2 Pa and 1.0 Pa, and the following mathematical procedure is followed. If the viscosity at a stress of 1 Pa is less than 75 Pa-sec, the zero shear viscosity is the median of the 4 highest viscosity values (i.e., individual points) obtained in the test, the yield stress is zero, and the following mathematical procedure is not used. The mathematical procedure is as follows. A straight line least squares regression is performed on the results using the logarithmically transformed data in the indicated stress region, an equation being obtained of the form:

$$\text{Log(strain)}=m*\text{Log(stress)}+b \quad (1)$$

Using the regression obtained, for each stress value (i.e., individual point) in the determination between 0.1 and 1,000 Pa, a predicted value of log(strain) is obtained using the coefficients m and b obtained, and the actual stress, using Equation (1). From the predicted log(strain), a predicted strain at each stress is obtained by taking the antilog (i.e., $10^x$ for each x). The predicted strain is compared to the actual strain at each measurement point to obtain a % variation at each point, using Equation (2).

$$\text{\% variation}=100*(\text{measured strain}-\text{predicted strain})/\text{measured strain} \quad (2)$$

The Yield Stress is the first stress (Pa) at which % variation exceeds 10% and subsequent (higher) stresses result in even greater variation than 10% due to the onset of flow or deformation of the structure.

The Young's Modulus (Pa) is obtained by graphing the stress (Pa) vs. strain (unitless). Young's modulus is derived from the slope of the regression line of the initial linear region between stress versus Strain graph. The multiphase personal care compositions of the present invention typically exhibit linear region in the strain range of 0 to about 0.05.

The Zero Shear Viscosity is obtained by taking a first median value of viscosity in Pascal-seconds (Pa-sec) for viscosity data obtained between and including 0.1 Pa and the Yield Stress. After taking the first median viscosity, all viscosity values greater than 5-fold the first median value and less than 0.2× the median value are excluded, and a second median viscosity value is obtained of the same viscosity data, excluding the indicated data points. The second median viscosity so obtained is the Zero Shear Viscosity.

The Shear Index (n) and Consistency Value (K):

The term "consistency value" or "k" as used herein is a measure of lipid viscosity and is used in combination with shear index, to define viscosity for materials whose viscosity is a function of shear. The measurements are made at 35° C. and the units are poise (equal to 100 cps). The term "shear index" or "n" as used herein is a measure of lipid viscosity and is used in combination with consistency value, to define viscosity for materials whose viscosity is a function of shear. The measurements are made at 35° C. and the units are dimensionless. The shear index (n) and consistency value (k) are known and accepted means for reporting the viscosity profile of materials having a viscosity that varies with applied shear rate using a Power Law model. The viscosity of a oil continuous benefit phase in a multiphase personal care composition can be measured by applying a shear stress and measuring the shear rate using a rheometer, such as a TA Instruments AR2000 (TA Instruments, New Castle, Del., USA 19720). Viscosity is determined at different shear rates in the following manner. First, an oil continuous benefit phase is obtained. If there exists more than one distinct, immiscible, benefit phase in the multiphase personal care composition, such as for example a silicone oil phase and a hydrocarbon phase, then the phase are either prepared separately and/or separated from each other, and evaluated separately from each other. In some embodiments, the oil continuous benefit phases which are mixtures, such as emulsions, are evaluated as mixtures, in addition to being evaluated individually.

For measurement, a 40 mm diameter parallel plate geometry with a gap of 1 mm is used unless there are particles in the multiphase personal care composition greater than 0.25 mm, in which case a gap of 2 mm is used. The rheometer uses standard parallel plate conventions to report shear rate at the edge as shear rate of the test; and converts torque to stress using the factor $2/(\pi R^3)$. Using a spatula, a sample comprising a small excess of the oil continuous benefit phase is loaded onto the rheometer base plate which is at 25° C., the gap is obtained, and excess composition outside the top measurement geometry is removed, locking the top plate in position during the removal of excess sample. The sample is equilibrated to the base plate temperature for 2 minutes. A preshear step is performed comprising 15 seconds of shear at a shear rate of 50 inverse seconds (1/sec). As is known to one skilled in the art, the shear rate with a parallel plate geometry is expressed as the shear rate at the edge, which is also the maximum shear rate. After the preshear step, the measurement is performed, which comprises ramping the stress from 10 Pa to 1,000 Pa over a 2.0 minute interval at 25° C., while collecting 60 viscosity data points, in an evenly spaced linear progression. A shear rate of at least 500 1/sec is obtained in the test, or the test is repeated with a fresh sample of the same component with a higher final stress value, maintaining the same rate of stress increase per time, until a shear rate of at least 500 1/sec is obtained during the measurement period. During the measurement, observe the sample to make certain the area under the top parallel plate is not evacuated of sample at any edge location during the measurement, or the measurement is repeated until a sample remains for the duration of the test. If after several trials a result cannot be obtained due to sample evacuation at the edge, the measurement is repeated leaving an excess reservoir of material at the edge (not scraping). If evacuation still cannot be avoided, a concentric cylinder geometry is used with a large excess of sample to avoid air pockets during loading. The results are fitted to the power law model by selecting only the data points between 25-500 l/sec shear rate, viscosity in Pa-s, shear rate in 1/sec, and using a least squares regression of the logarithm of viscosity vs. the logarithm of shear rate to obtain values of K and n according to the Power Law equation:

$$\mu = K(\gamma)^{(n-1)}$$

The value obtained for the log-log slope is (n−1) where n is the Shear Index and the value obtained for K is the Consistency Value, expressed in units of in Pa-s.

The "Third-Phase" Method for Determining Structured Surfactant Stability:

The "Third-Phase" Method is used to determine structured surfactant phase stability in a multiphase personal care composition. The method involves separation of the c multiphase personal care composition through ultracentrifugation into separate but distinguishable layers. The multiphase personal care composition of the present invention can have multiple distinguishable layers, for example an opaque structured surfactant layer, a clear "third-phase" layer, and oil continuous benefit phase layers.

First, samples of the multiphase personal care composition care aged using a rapid stability aging protocol involves placing the sample of the multiphase personal care composition at 120° F. (48.9° C.) for 10 days. After the rapid stability aging protocol, about 4 grams of sample of the multiphase personal care composition is dispersed into centrifuge tubes, such as a Beckman Coulter centrifuge tube that is 11 mm by 60 mm. The centrifuge tubes are placed in an ultracentrifuge, such as Ultracentrifuge OPTIMA™ L-80 (Beckman Instruments, Inc., Fullerton, Calif.). The samples are centrifuged at 50,000 rpm at 40° C. for 2 hours.

After ultracentrifugation, the third-phase volume of a sample is determined by measuring the height of various surfactant phases using an Electronic Digital Caliper (within 0.01 mm) as shown below. An example is shown below for a multiphase personal care composition comprising EXCANCEL™ low density microspheres, petrolatum, mineral oil and a structured surfactant phase.

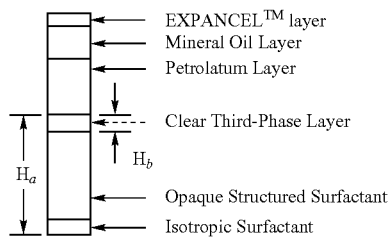

When a density modifier such as EXPANCEL™ low density microspheres is used, the very top layer primarily comprises the EXPANCEL™ low density microspheres. The second layer from the top is the clear mineral oil layer. The third layer from the top is the petrolatum layer. The layers below the petrolatum layers contain aqueous surfactant and are characterized as follows: $H_a$ is the height of all the aqueous and/or aqueous surfactant layers and $H_b$ is the height of the clear "third-phase" layer just below the petrolatum layer. It is important to record the readings within 30 minutes after the Ultracentrifugation is finished to minimize material migration. The third phase volume is calculated as: Third-phase Volume %=$H_b/H_a$*100%

In some embodiments, the structured surfactant phase composition comprises less than 5% "third-phase" volume after rapid aging protocol. In other embodiments, the structured surfactant phase composition comprises less than 2% "third-phase" volume after rapid aging protocol. In other embodiments, the structured surfactant phase composition comprises less than 1% "third-phase" volume after rapid aging protocol.

Figure 2:
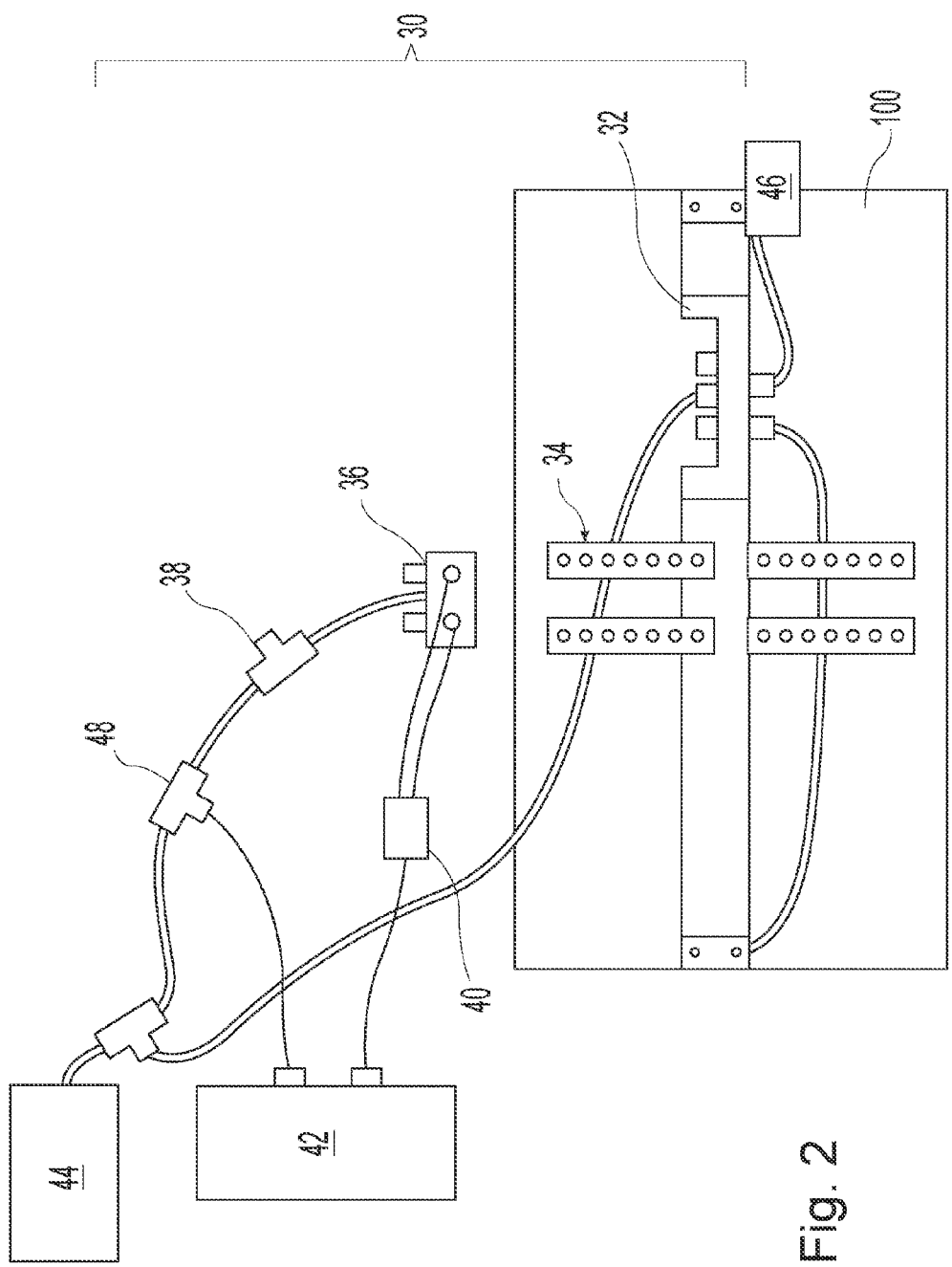
FIG. 2 is a top view of the automated cleansing unit used in the in vitro deposition method.

In-Vitro Deposition Method:

The In-Vitro deposition method measures the deposition of benefit agents on a mechanically stressed skin mimic. The method compares spectral data of the skin mimic surface material before and after cleansing in an automated cleansing unit, such as shown in FIG. 1, FIG. 2 and FIG. 3.

The In-Vitro deposition method uses two 96-well microplates (hereinafter referred to as "microplates"). Suitable 96-well microplates are commercially available from PerkinElmer and from VWR.com. For example, the SpectraPlate 96-MG from PerkinElmer has 8 rows and 12 columns with a well volume of 400 μl. The SpectraPlate 96-MG comprises the approximate dimensions of 14.6 mm in height, 127.8 mm in length and 85.5 mm in width. The SpectraPlate 96-MG has a well diameter of 7.15 mm, a well depth of 10.8 and a well to well spacing of 9.0 mm. A 96-well microplate is provided for containing the samples comprising the personal care composition in the Examples below The in-vitro deposition method uses approximately 1536 bodies. Each body are approximately 2 mm in circumference spherical stainless steel bearings that comprise ferrometallic material, such as those available from WLB Antriebeselemente Gmbh, Scarrastrasse 12, D-68307 Mannheim, Germany. Eight bodies carefully loaded into each of the 96 wells of microplates to ensure the same number is loaded into each well.

Before samples are prepared, the personal care compositions are prepared according to the description in the Example Section below. After the examples of the personal care compositions are prepared, samples are prepared by combining a personal care composition and distilled water, For each sample, 90±0.02 grams of distilled water is dispensed into a mixing vessel. The mixing vessel is secured to the base of a mixer, such as a table top mixer from IKA, the mixer blades are adjusted into the distilled water within the mixing vessel. A syringe is then zeroed on a balance. The syringe is filled with the designated personal care composition. The syringe is weighed and small amounts of the designated personal care composition are dispensed until 10 grams of the personal care composition remains in the syringe. The mixer is turned on at a speed of 500 rpm and the contents of the syringe are dispensed into distilled water within the mixing vessel. The distilled water and the designated personal care composition are mixed for 2 minutes at 500 rpm forming the sample. The sample is withdrawn by syringe from the mixing vessel while the mixer is on at a speed of 300 rpm. The mixing and dispensing procedures are followed for mixing and dispensing for the control sample and the test samples 1-5. After the samples are prepared, the control samples and test samples are dispensed in the specified wells of the microplate.

The skin mimic used in the in-vitro deposition methods is comprised of a molded bicomponent polyethylene substrate. The skin mimic is textured on one side with a pattern that resembles the texture of human skin. The textured side of the skin mimic is coated with 1,1,1-trimethyl-1-pentene that is plasma deposited. The skin mimic has a total surface energy of $32\pm1.0$ (mJ/m$^2$), a zeta potential of $(-)$ 27.4 (mV), a contact angle in water of $100°\pm2.0$.

The preparation of the skin mimic comprises the steps of preparing the metallic mold (a), forming the substrate of the skin mimic (b) and formation of the treated test mimic of the skin mimic.

(a) Metallic Mold Preparation: A pattern resembling the texture of human forearm skin is formed from a photograph image of human forearm skin. The pattern is transferred to a clear sheet to form a mask. A DuPont™ MX series dry film photoresists is adhered to the metal sheet. The mask is placed on top of the metal sheet to form a metal/photoresist/mask. The composite of metal/photoresist/mask is exposed to an appropriate dose of UV light, using industry standard exposure tools. The mask is removed, the photoresist is developed and the metal sheet is etched using appropriate etching solutions, as described in standard textbooks on second level microelectronics packaging. For example, Donald Seraphim, Ronald Lasky and Che-Yu Li, Principles of Electronic Packaging, Mc-Graw Hill Inc. (1989).

(b) Formation of the Substrate of the Skin Mimic: A 1:1 mixture of Skin-Flex SC-89 Stretch-paint and Skin-Flex SC-89 Thinner S4 SC-89 Thinner, both available from Burman Industries, (Van Nuys, Calif.) is poured into the prepared metallic mold and allowed to dry overnight. The amount of the mixture poured is adjusted according to the size of the mold, to yield a final substrate that is typically between 600 to 800 micrometers thick. After overnight drying, the substrate material is carefully peeled off of the metallic mold.

(c) Formation of the treated test region of skin mimic. The plasma deposition is performed in a plasma unit, between the two electrodes, by application of the continuous wave radiofrequency (hereinafter referred to as "RF") power. The effective plasma treatment area is approximately 40 cm by 20 cm. The plasma unit comprises a cylindrical vacuum chamber having a diameter of approximately 30.5 cm and a length of 61.0 cm. Vacuum is produced by means of a LEYBOLD™ PCS 25 vacuum pump. The RF energy is supplied from a PE 1000 ADVANCED ENERGY™ 40 KHz power supply, across a set of parallel aluminum electrodes in the vacuum chamber. The substrate is placed on a perforated aluminum sample tray in between parallel plate aluminum electrodes in the vacuum chamber and the vacuum chamber pressure is reduced to approximately 100 milliTorr (mTorr). The substrate to be plasma coated is substantially degassed by adding a mixture of argon and nitrogen gas into the vacuum chamber at flow rates of 20 sccm of argon and 10 sccm of nitrogen, (where "sccm" means standard cubic centimeter per minute) for about one hour. After the substrate is degassed for one hour, the vacuum chamber pressure is reduced to 10 mTorr and 25 W of continuous wave RF power is applied for approximately 5 minutes while allowing the argon/nitrogen gas mixture to flow into the vacuum chamber at flow rates of 20 sccm of argon and 10 sccm of nitrogen. After 5 minutes, the release of gas is stopped and vacuum chamber is evacuated to the pressure of 10 mTorr. The 1,1,1-trimethyl-1-pentene coating material available from Aldrich is introduced into the vacuum chamber to a pressure of 100 mTorr at a flow rate selected is from about 10 sccm to 200 sccm depending the knowledge of or may be determined with limited experimentation by one of ordinary skill in the art. While the coating material is introduced into the vacuum chamber 25 W of continuous wave RF power is applied for approximately 25 minutes while maintaining a vapor pressure of approximately 100-120 mTorr. The plasma deposition results in a polymeric coating of 1,1,1-trimethyl-1-pentene that is covalently bonded to the substrate. The exact times for plasma deposition will be within the knowledge or may be determined with limited experimentation by one of skill in the art. After 25 minutes, the power to the plasma unit is turned off and the flow of the coating material is stopped. The vacuum chamber is purged with about 20 sccm argon for about 30 min prior to the removal of the coated substrate. The plasma coated substrates are removed from the chamber the contact angle, the surface charge and the thickness of the coating layer is determined by video contact angle measurement system (VCA-2500 from ASM), zeta-potential measurement (Anton Parr Electrokinetic Analyzer, Model BI-EKA) and Atomic Force Microscopy (Q-Scope 250 from Quesant Corporation) methods. However, one of skill in the art will understand that a variety of coating materials, as described herein, may be used, the choice of which will be determined by the surface property of the keratinous tissue that one desires to reproduce.

After all of the wells of the microplate are filled with the samples and the pieces of skin are made and coated, the skin mimic is prepared for the in vitro deposition method. Two pieces of skin mimic are prepared by cutting the skin mimic to fit on top of the openings of the wells of the microplate while wearing gloves. The two pieces of skin mimic pieces are numbered "1" and "2".

A base line spectral data was obtained by the spectrophotometer for both pieces of skin mimic. An Eye-one® IO Spectrophotometer from GretagMacbeth with Measure Tool Software (collectively hereinafter referred to as "spectrophotometer") and a computer associated with the spectrophotometer (hereinafter referred to as "computer") was utilized. The reading surface of the spectrophotometer is cleaned prior to each reading. The reading surface of the spectrophotometer is black in order to provide adequate reflection. The first piece of skin mimic is placed on the reading surface with the textured and treated region of the skin mimic facing the spectrophotometer. Next, a piece of plastic having a plurality of holes which correspond in size to the openings of the microplate is placed over the textured and treated region of the skin mimic. A scan is then performed using the robot arm of the spectrophotometer. The baseline spectral data for the first piece of skin mimic is saved on a computer as the first baseline. The reading surface of the spectrophotometer is cleaned and the spectral data for the second piece of skin mimic surface is, as described for the first piece of skin mimic. The baseline spectral data for the second piece of skin mimic is saved on the computer as the second baseline.

Next, the pieces of skin mimics are arranged over the openings of the wells of the microplates. The pieces of skin mimic surface material are transferred to cover the openings of the wells of the each of the microplates to ensure that the textured and treated region of the skin mimic is facing the openings of the wells of the microplate. A lid is placed over each piece of the skin mimic and the associated microplate to form a lidded microplate.

The next step is to place the lidded microplates into the microplate holders 20 of automated cleansing unit 100. FIG. 1 is an isometric view of the automated cleansing unit 100, a 21 device used in the in vitro method of the present invention. The automated cleansing unit 100 is comprises a horizontal base 18 comprising four microplate holders 20. The horizontal base 18 is made of rectangle of aluminum comprising the following approximate dimensions of ⅜ inch in height, fourteen inches in width and twenty seven inches in length. The automated cleansing unit 100 comprises two vertical supports 22 comprised of aluminum with the approximate dimensions of one inch by two inches by ten and ¾ of an inch in height. The vertical supports 22 are attached to a horizontal support comprising a rodless air slide 24. The horizontal support comprising a rodless air slide 24 comprises the approximately dimension of a ½ inch by two inches by twenty six and ½ inches in height. Suitable rodless air slides 24 comprise a one inch bore and eleven inch stroke and have associated end lugs and mount brackets, which are commercially available from McMaster-Carr. The rodless air slide 24 is double acting and comprises a carriage that is connected to an internal piston and two compressed air ports (not shown).

The automated cleansing unit 100 comprises two magnetic arms 26. The horizontal support comprising a rodless air slide 24 is the structure upon which the two magnetic arms 26 are mounted. The magnetic arms 26 are mounted to the rodless air slide 24 such that the magnetic arms 26 move back and forth along the length of the double acting rodless air slide 24 by the force of compressed air. Each of the magnetic arms 26 are comprised of aluminum and have the approximate dimensions of one inch by two inches by fourteen inches in length and have a "T" shape channel that houses seven neodymium iron boron magnets (not shown). Each of the neodymium iron boron magnets have the approximate dimensions of two inches in length, one inch in width and half or an inch in height. Each of the neodymium iron boron magnets comprise a magnetic strength of 12200 Gauss, available from Edmund Scientifics. The magnetic arms 26 are configured at a height of about 2.75 cm above the microplate holder 20 with the caveat that the magnets maintain their function to attract and move the bodies comprised within the wells of the microplate. The magnetic arms 26 move back and forth along the length of the rodless air slide 24 by the force of compressed air at a speed of approximately 6 back and forth sweeps over the length of the rodless air slide 24 over a 10 second time period.

Below the magnetic arms 26 are configured four microplate holders 20. Each of the microplate holders 20 comprise a clamping plate 60 and four pistons 28 attached to a pneumatic control unit 30. When actuated, the pistons 28 for the pneumatic control unit 30 hold the microplates in the four microplate holders 20 at a pressure of from about 90 psi. Prior to placing the lidded microplates into the microplate holders 20 of automated cleansing unit 100, the pneumatic control unit 30 is turned on.

FIG. 2 is a top view of the automated cleansing unit 100 comprising one embodiment of the pneumatic control unit 30. The top view shows components of the pneumatic control unit 30 which are connected to the rodless air slide 24, the piston 28 and clamping plates 60 shown in FIG. 1. The pneumatic control unit 30 is used to apply compressed air to the automated cleansing unit 100, which imparts a force by converting the potential energy of compressed air into kinetic energy. The pneumatic control unit 30 comprises a solenoid air control valve 32, a distribution manifold outlet 34, a compressed air control valve 36, a compressed air flow regulator 38, an alternating output binary valve 40, a two-hand safety pneumatic control valve 42, a compressed air control valve 46 and various connectors 48 that provide pressurized air to the automated cleansing unit 100 from an external air source 44. The air control valve 36, air flow regulators 38, alternating a binary valves 40, a two-hand safety pneumatic control valve 42 are positioned upstream of a solenoid air control valve 32. A suitable solenoid air control valve, in one embodiment, is described as a double air style valve with a 10 psi to 120 operating pressure. Suitable compressed air flow regulators 38, in some embodiments, operate in the pressure range of 14 psi to 116 psi. Suitable air control valve alternating output binary valves 40, in some embodiments, operate in a 35 psi to 100 psi range. All of the components of the pneumatic control unit 30 are available from McMaster-Carr®.

A detailed cut away side view of the microplate holder 20 is shown in FIG. 3. The microplate holder 20, in one embodiment, is designed to hold four commercially available 96 well microplates. The microplate holder 20 comprises a riser 50, an aluminum base plate 54, a clamping plate 60 and pistons 28. Riser 50 has a larger dimension than the approximately dimension of a commercially available microplate. In some embodiments, the riser 50 has the dimensions of inches by five inches by five and ¾ inches. The riser 50 is comprised of polyoxymethylene which is commonly known under DuPont's brand name DELRIN®. DELRIN® is used as a metal substitute because it is a lightweight, low-friction, and wear-resistant thermoplastic that possesses good physical and processing properties and capable of operating in temperatures in excess of 90° C. In addition to the riser 50, the microplate holder, in some embodiments, comprises an aluminum base plate 54. The aluminum base plate 54 has a raised portion 56 and a trench 58 which is approximately the same dimensions as a commercially available microplate, such that the bottom of the wells rest on the raised portion 56 and the perimeter of the microplate fits in the trench 58. The aluminum base plate 52 is designed such that the microplate is not adversely affected by the compression of the clamping plate 60 by the piston 28 when the pneumatic pressure unit 30 is actuated.

The aluminum base plate 54 comprises a first heater 52 and the clamping plate 60 comprises a second heater 62. The first heater 52 and second heater 62 comprise flexible silicone rubber heaters available from Omega.com. The first heater 52 and the second heater 62 can be controlled, in some embodiments, by a ¼ DIN six zone temperature controller with RS-232 communications and free configuration software available by from Omega.com. The first heater 52 and the second heater 62 are used to stabilize the temperature of the sample and the skin mimic at room temperature ranging from about 20° C. to about 25° C. Prior to placing the lidded microplates into the microplate holders 20 of automated cleansing unit 100, the first heater 52 and the second heater 62 are turned on to stabilize the temperature of the sample and the skin mimic at room temperature ranging from about 20° C. to about 25° C.

The lidded microplates are placed into the microplate holders 20 and pneumatic control unit 30 is actuated such that the lidded microplates are held under 90 psi of pressure. The magnetic arms 26 are actuated on and arms moves over the lidded microplates at a height of 2.65 cm above the microplate holders 20. The magnetic arms 26 of the automated cleansing unit 100, sweep back and forth over the microplate holders 20 for 5 minutes, at a speed of 6 sweeps per every 10 seconds. After 5 minutes of the automated cleansing process, the lidded microplates are removed from the microplate holders 20 and are disassembled so that spectral data is gathered by a spectrophotometer for both pieces of skin mimic surface material.

Prior to the spectral readings, two large 4000 ml beakers of 20° C. to 25° C. water are filled. The first piece of skin mimic is removed from the first microplate and submerged in the tap water within the first beaker five times. The second piece of skin mimic is removed from the second microplate and submerged within the second beaker five times. The completeness of rinsing step is judged visually by the lack of foam on the skin mimic and presence of defined circles of deposited material on the skin mimic. Both piece of skin mimic are blotted with paper towels and fumed in a drying hood for five minutes each. The reading surface of the spectrophotometer is cleaned. The first piece of skin mimic is placed on the reading surface with the textured and treated region of the first skin mimic facing the spectrophotometer. Next, a piece of plastic having a plurality of holes which correspond in size to the openings of the microplate is placed over the textured and treated region of the first skin mimic. The scan is then performed using the robot arm of the spectrophotometer. The baseline spectral data for the first piece of skin mimic material is saved for comparison with the first baseline. The reading surface of the spectrophotometer is cleaned and the spectral data for the second piece of skin mimic surface material is obtained by the aforesaid method. The baseline spectral data for the second skin mimic surface material is saved on a computer for comparison with the second baseline.

The spectrophotometer measures the L-a-b values for the skin mimic surface material before cleansing and after washing. The deposition values of the in-vitro method are reported as a Delta L value and are indicative of the deposition profile of each sample. The difference of the light intensity L or "Delta-L" is the L value after the cleansing-L value before cleansing (the baseline spectral data).

EXAMPLES

The following examples further describe and demonstrate embodiments within the scope of the invention. The examples are given solely for the purpose of illustration and are not to be construed as limitations of the present invention, as many variations thereof are possible without departing from the spirit and scope of the invention.

Comparative Examples A, B and C are prepared by the following procedure: First, a citric solution is prepared by adding citric acid and distilled water into a first mixing vessel at a ratio of 50:50. Acrylates/vinyl isodecanoate is added to a second mixing vessel with water while mixing. Sodium hydroxide is added to the second mixing vessel and the pH of the mixture is adjust to about 7. Sodium lauroamphoacetate, sodium lauryl sulfate, and sodium trideceth sulfate, sodium chloride, trideceth-3, EDTA, sodium benzoate, guar hydroxypropyltrimonium chloride is added to the second mixing vessel. The pH of the mixture in the second mixing vessel is adjusted to 5.7±0.2 using the citric acid solution. Perfume and methyl chloro isothiazolinone and methyl isothiazolinone is added and mixed into the second mixing vessel until homogeneous forming the structured surfactant phase. The oil continuous benefit phase is prepared by adding petrolatum into a third mixing vessel while heating the third mixing vessel to about 88° C. Mineral and titanium dioxide are added to the third mixing vessel with mixing. The mixture in the third mixing vessel is then cooled to 45° C. with agitation. At 45° C., the agitation is stopped and the mixture in the third mixing vessel is cooled to room temperature. The oil continuous benefit phase is blended with structured surfactant phase at a specified ratio using a SpeedMixer™ (from FlackTek Inc.) at 2800 rpm for 1 min. Comparative Examples A, B and C are subjected to the in-vitro deposition evaluation method, as described in the Test Methods above.

Comparative Examples A, B and C illustrate the impact of cationic polymer on deposition, as measured by the in-vitro deposition evaluation method. Comparative examples A, B and C demonstrate that there is competition between the deposition of the benefit material and the cocervate in typical

TABLE 2

Comparative Examples A, B and C

| Ingredients: | Comparative Examples | | |
|---|---|---|---|
| | A | B | C |
| I: Structured surfactant phase Composition | | | |
| sodium trideceth sulfate, sulfated to >95% from ICONOL ™ TDA-3 tridecyl alcohol alkoxylate (BASF Corp.) | 5.9 | 5.9 | 5.9 |
| sodium lauryl sulfate (Procter & Gamble) | 5.9 | 5.9 | 5.9 |
| sodium lauroamphoacetate (Cognis Corp.) | 3.6 | 3.6 | 3.6 |
| guar hydroxypropyltrimonium chloride (N-HANCE ® from Aqualon) | — | 0.3 | 0.7 |
| acrylates/vinyl isodecanoate (STABYLEN ® 30 from 3V Sigma) | 0.33 | 0.33 | 0.33 |
| sodium chloride | 3.75 | 3.75 | 3.75 |
| trideceth-3 (ICONOL ™ TDA-3I from BASF Corp.) | 1.75 | 1.75 | 1.75 |
| methyl chloro isothiazolinone and methyl isothiazolinone (KATHON ™ CG from Rohm & Haas) | 0.033 | 0.033 | 0.033 |
| Ethylenediaminetetraacetic acid (DISSOLVINE NA 2x from Akzo Nobel) | 0.15 | 0.15 | 0.15 |
| sodium benzoate | 0.2 | 0.2 | 0.2 |
| citric acid, titrated to a pH of | 5.7 ± 0.2 | 5.7 ± 0.2 | 5.7 ± 0.2 |
| Perfume | 1.11 | 1.11 | 1.11 |
| water and minors (NaOH) | Q.S. | Q.S. | Q.S. |
| II: Oil continuous benefit phase Composition | | | |
| petrolatum (G2218 from Sonnerbonn) | 65 | 65 | 65 |
| mineral oil (HYBROBRITE ® 1000 from Sonnerbonn) | 25 | 25 | 25 |
| titanium oxide (RBTD-834-11S2 from Kobo Products) | 10 | 10 | 10 |
| III: structured surfactant phase:oil continuous benefit phase blending ratio | 90:10 | 90:10 | 90:10 |
| In-vitro Deposition of Comparative Examples A, B and C | | | |
| Delta L | 11.56 | 7.4 | 3.2 |
| Percent Difference in Delta L from Control | Control | −36% | −73% | personal care compositions. The structured surfactant phase of comparative example A, which acts as the control, does not comprise a cationic deposition polymer. The structured surfactant phase in comparative example B comprises 0.3%, by weight of the multiphase personal care composition, of cationic polymer. The structured surfactant phase in comparative example B comprises 0.6%, by weight of the multiphase personal care composition of cationic deposition polymer. The results of percent difference in the Delta L values from control show a decrease in deposition of 36% and 73% as compared to the control.

chloro isothiazolinone and methyl isothiazolinone is added and mixed into the second mixing vessel until homogeneous forming the structured surfactant phase. The oil continuous benefit phase is prepared by adding petrolatum into a third mixing vessel while heating the third mixing vessel to about 88° C. Glyceryl monooleate is added to the third mixing vessel. Gycerin is added slowly to the third mixing vessel with mixing. Titanium dioxide is added to the third mixing vessel with mixing. The mixture in the third mixing vessel is then cooled to 45° C. with agitation. At 45° C., the agitation is stopped and the mixture in the third mixing vessel is cooled to

TABLE 3

Comparative Examples D, E and F and Inventive Examples 1 and 2

| Ingredients: | Comparative Examples | | | Inventive Examples | |
|---|---|---|---|---|---|
| | D | E | F | 1 | 2 |
| I: Structured surfactant phase composition | | | | | |
| sodium trideceth sulfate, sulfated to >95% from ICONOL ™ TDA-3 tridecyl alcohol alkoxylate (BASF Corp.) | 8.5 | 8.5 | 8.5 | 8.5 | 8.5 |
| sodium lauryl sulfate (Procter & Gamble) | 8.5 | 8.5 | 8.5 | 8.5 | 8.5 |
| sodium lauroamphoacetate (Cognis Corp.) | 5 | 5 | 5 | 5 | 5 |
| guar hydroxypropyltrimonium chloride (N-HANCE ® 3196 from Aqualon) | — | — | — | 0.6 | — |
| guar hydroxypropyltrimonium chloride (JAGUAR ® C-17 from Rhodia) | — | — | — | — | 0.6 |
| hydroxyproypl guar hydroxypropyltrimonium chloride (Aqua D3531 from Aqualon) | — | 0.6 | — | — | — |
| Polyquaterium-10 (JR-30M Polymer from Amerchol) | — | — | 0.6 | — | — |
| sodium chloride | 4.75 | 4.75 | 4.75 | 4.75 | 4.75 |
| trideceth-3 (ICONOL ™ TDA-3I from BASF Corp.) | 2 | 2 | 2 | 2 | 2 |
| methyl chloro isothiazolinone and methyl isothiazolinone (KATHON ™ CG from Rohm & Haas) | 0.033 | 0.033 | 0.033 | 0.033 | 0.033 |
| Ethylenediaminetetraacetic acid (DISSOLVINE NA 2x from Akzo Nobel) | 0.15 | 0.15 | 0.15 | 0.15 | 0.15 |
| sodium benzoate | 0.2 | 0.2 | 0.2 | 0.2 | 0.2 |
| perfume | 1.8 | 1.8 | 1.8 | 1.8 | 1.8 |
| citric acid, titrated to a pH of | 5.7 ± 0.2 | 5.7 ± 0.2 | 5.7 ± 0.2 | 5.7 ± 0.2 | 5.7 ± 0.2 |
| water and minors (NaOH) | Q.S. | Q.S. | Q.S. | Q.S. | Q.S. |
| II: Oil continuous benefit phase composition | | | | | |
| petrolatum (G2218 from Sonnerbonn) | 65.3 | 65.3 | 65.3 | 65.3 | 65.3 |
| glycerol monooleate, with an HLB of 3.8 (MONOMULS ® 90-0 18 from Cognis) | 1.9 | 1.9 | 1.9 | 1.9 | 1.9 |
| glycerin | 28.8 | 28.8 | 28.8 | 28.8 | 28.8 |
| titanium oxide (RBTD-834-11S2 from Kobo Products) | 4 | 4 | 4 | 4 | 4 |
| III: ratio of structured surfactant phase:oil continuous benefit phase blending ratio | 50:50 | 50:50 | 50:50 | 50:50 | 50:50 |
| IV: ratio of hydrocarbon benefit material:low HLB emulsifier | 34:1 | 34:1 | 34:1 | 34:1 | 34:1 |
| In-vitro Deposition of Comparative Examples D, E and F and Inventive Examples 1 and 2 | | | | | |
| Delta L | 3.31 | 0.54 | 0.72 | 12.57 | 17.40 |
| Percent Difference in Delta L from Control | Control | −84% | −78% | +278% | +425% |

Comparative Examples D, E and F and Inventive Examples 2 and 3 are prepared by the following procedure: First, a citric solution is prepared by adding citric acid and distilled water into a first mixing vessel at a ratio of 50:50. In a second mixing vessel, add cationic polymer (Comparative Examples E and F and Inventive Examples 2 and 3) to water with agitation. Add sodium lauroamphoacetate, sodium lauryl sulfate, sodium trideceth sulfate, trideceth-3, sodium chloride, EDTA, sodium benzoate to the second mixing vessel. The pH of the mixture in the second mixing vessel is adjusted to 5.7±0.2 using the citric acid solution. Perfume and methyl room temperature. The oil continuous benefit phase is blended with structured surfactant phase at a specified ratio using a SpeedMixer™ (from FlackTek Inc.) at 2800 rpm for 1 min. Comparative Examples D, E and F and Inventive Examples 1 and 2 are subjected to the in-vitro deposition evaluation method, as described in the Test Methods above.

Comparative Examples D, E and F and Inventive Examples 1 and 2 illustrate the impact of the cationic polymer on deposition, as measured by the in-vitro deposition evaluation method. The structured surfactant phase of comparative example D, which acts as the control, does not comprise a cationic deposition polymer. Inventive Examples 1 and 2 comprise structured surfactant phase comprising a cationic guar. The percent difference in Delta L values versus control of Inventive Examples 1 and 2 and Comparative Example E and F show the importance of the cationic deposition polymer structure for an increase in deposition. It is evident that the inventive Example 1 and 2 delivers a significant increase in deposition utilizing a cationic guar as compared to control.

vessel. Gycerin is added slowly to the third mixing vessel with mixing. Titanium dioxide is added to the third mixing vessel with mixing. The mixture in the third mixing vessel is then cooled to 45° C. with agitation. At 45° C., the agitation is stopped and the mixture in the third mixing vessel is cooled to room temperature. The oil continuous benefit phase is blended with structured surfactant phase at a specified ratio using a SpeedMixer™ (from FlackTek Inc.) at 2800 rpm for

TABLE 4

Comparative Examples G and H and Inventive Examples 3 and 4

|  | Comparative Examples | | Inventive Examples | |
| --- | --- | --- | --- | --- |
|  | G | H | 3 | 4 |
| I: Structured surfactant phase composition |  | 8.5 | 8.5 | 8.5 |
| sodium trideceth sulfate, sulfated to >95% from ICONOL ™ TDA-3 tridecyl alcohol alkoxylate BASF Corp.) | 8.5 | 8.5 | 8.5 | 8.5 |
| sodium lauryl sulfate (Procter & Gamble) | 8.5 | 5 | 5 | 5 |
| sodium lauroamphoacetate (Cognis Corp.) | 5 | — | 0.6 | — |
| guar hydroxypropyltrimonium chloride (JAGUAR ® C-17 from Rhodia) | — | — | — | 0.6 |
| guar hydroxypropyltrimonium chloride (JAGUAR ® Excel from Rhodia) | — | — | 0.6 | — |
| hydroxypropyl guar hydroxypropyltrimonium chloride(ADPP-7361 from Aqualon) | — | 0.6 | — | — |
| sodium chloride | 4.75 | 4.75 | 4.75 | 4.75 |
| trideceth-3 (ICONOL ™ TDA-3I from BASF Corp.) | 2 | 2 | 2 | 2 |
| methyl chloro isothiazolinone and methyl isothiazolinone (KATHON ™ CG from Rohm & Haas) | 0.033 | 0.033 | 0.033 | 0.033 |
| ethylenediaminetetraacetic acid (DISSOLVINE NA 2x from Akzo Nobel) | 0.15 | 0.15 | 0.15 | 0.15 |
| sodium benzoate | 0.2 | 0.2 | 0.2 | 0.2 |
| perfume | 1.8 | 1.8 | 1.8 | 1.8 |
| citric acid, titrated to a pH of | 5.7 ± 0.2 | 5.7 ± 0.2 | 5.7 ± 0.2 | 5.7 ± 0.2 |
| water and minors (NaOH) | Q.S. | Q.S. | Q.S. | Q.S. |
| II: Oil continuous benefit phase composition |  |  |  |  |
| Petrolatum (G2218 from Sonnerbonn) | 65.3 | 65.3 | 65.3 | 65.3 |
| glycerol monooleate, with an HLB of 3.8 (MONOMULS ® 90-0 18 from Cognis) | 28.8 | 28.8 | 28.8 | 28.8 |
| glycerin | 1.9 | 1.9 | 1.9 | 1.9 |
| titanium oxide (RBTD-834-11S2 from Kobo Products) | 4 | 4 | 4 | 4 |
| III: ratio of structured surfactant phase:oil continuous benefit phase blending ratio | 50:50 | 50:50 | 50:50 | 50:50 |
| IV: ratio of hydrocarbon benefit material:low HLB emulsifier | 49:1 | 49:1 | 49:1 | 49:1 |
| In-vitro Deposition of Comparative Examples G and H and Inventive Examples 2 and 3 | | | | |
| Delta L | 2.15 | 1.49 | 12.20 | 14.50 |
| Percent Difference of Delta L from Control | Control | −30% | +467% | +574% |

Comparative Examples G and H and Inventive Examples 2 and 3 are prepared by the following procedure: First, a citric solution is prepared by adding citric acid and distilled water into a first mixing vessel at a ratio of 50:50. In a second mixing vessel, add cationic polymer (Comparative Example H and Inventive Examples 2 and 3) to water with agitation. Add sodium lauroamphoacetate, sodium lauryl sulfate, sodium trideceth sulfate, trideceth-3, sodium chloride, EDTA, sodium benzoate to the second mixing vessel. The pH of the mixture in the second mixing vessel is adjusted to 5.7±0.2 using the citric acid solution. Perfume and methyl chloro isothiazolinone and methyl isothiazolinone is added and mixed into the second mixing vessel until homogeneous forming the structured surfactant phase. The oil continuous benefit phase is prepared by adding petrolatum into a third mixing vessel while heating the third mixing vessel to about 88° C. Glyceryl monooleate is added to the third mixing 1 min. Comparative Examples G and H and Inventive Examples 2 and 3 are subjected to the in-vitro deposition evaluation method, as described in the Test Methods above.

Comparative Examples G and H and Inventive Examples 2 and 3 illustrated the impact of the cationic polymer on deposition, as measured by the in-vitro deposition evaluation method. The structured surfactant phase of comparative example G, which acts as the control, does not comprise a cationic polymer. Comparative Example H comprises a hydropropyl guar hydroxypropyltrimonium chloride. The results in the percent difference in Delta L from control in Table 4 show Inventive Examples 2 and 3 deliver increased deposition enhancement utilizing guar hydroxypropyltrimonium chloride, as compared to control Comparative Example G.

TABLE 5

Comparative Example I and Inventive Examples 5 and 6

| | Comparative Example | Inventive Examples | |
|---|---|---|---|
| | I | 5 | 6 |
| I: Structured surfactant phase Composition | | | |
| sodium trideceth sulfate, sulfated to >95% from ICONOL ™ TDA-3 tridecyl alcohol alkoxylate (BASF Corp.) | 8.5 | 8.5 | 8.5 |
| sodium lauryl sulfate (Procter & Gamble) | 8.5 | 8.5 | 8.5 |
| sodium lauroamphoacetate (Cognis Corp.) | 5 | 5 | 5 |
| guar hydroxypropyltrimonium chloride (JAGUAR ® Excel from Rhodia) | 0.6 | 0.6 | 0.6 |
| sodium chloride | 4.75 | 4.75 | 4.75 |
| trideceth-3 (ICONOL ™ TDA-3I from BASF Corp.) | 2 | 2 | 2 |
| methyl chloro isothiazolinone and methyl isothiazolinone (KATHON ™ CG from Rohm & Haas) | 0.033 | 0.033 | 0.033 |
| ethylenediaminetetraacetic acid (DISSOLVINE NA 2x from Akzo Nobel) | 0.15 | 0.15 | 0.15 |
| sodium benzoate | 0.2 | 0.2 | 0.2 |
| perfume | 1.8 | 1.8 | 1.8 |
| Citric acid, titrated to a pH of | 5.7 ± 0.2 | 5.7 ± 0.2 | 5.7 ± 0.2 |
| Water and minors (NaOH) | Q.S. | Q.S. | Q.S. |
| II: Oil continuous benefit phase Composition | | | |
| petrolatum (G2218 from Sonnerbonn) | 63.7 | 66.5 | 65.8 |
| glycerol monooleate, with an HLB of 3.8 (MONOMULS ® 90-0 18 from Cognis) | 27.3 | 28.5 | 28.2 |
| glycerin | 5 | 1 | 2 |
| titanium oxide (RBTD-834-11S2 from Kobo Products) | 4 | 4 | 4 |
| III: ratio of structured surfactant phase:oil continuous benefit phase blending ratio | 50:50 | 50:50 | 50:50 |
| IV: ratio of hydrocarbon benefit material:low HLB emulsifier | 18:1 | 95:1 | 49:1 |
| In-vitro Deposition of Comparative Example I and Inventive Examples 5 and 6 | | | |
| Delta L | 6.8 | 11.5 | 12.8 |
| Percent Difference of Delta L from Control | Control | +69% | +88% |
| Lather Performance | Poor | Excellent | Excellent |

Comparative Example I and Inventive Examples 5 and 6 are prepared by the following procedure: First, a citric solution is prepared by adding citric acid and distilled water into a first mixing vessel at a ratio of 50:50. In a second mixing vessel, add cationic polymer to water with agitation. Add sodium lauroamphoacetate, sodium lauryl sulfate, sodium trideceth sulfate, trideceth-3, sodium chloride, EDTA, sodium benzoate to the second mixing vessel. The pH of the mixture in the second mixing vessel is adjusted to 5.7±0.2 using the citric acid solution. Perfume and methyl chloro isothiazolinone and methyl isothiazolinone is added and mixed into the second mixing vessel until homogeneous forming the structured surfactant phase. The oil continuous benefit phase is prepared by adding petrolatum into a third mixing vessel while heating the third mixing vessel to about 88° C. Glyceryl monooleate is added to the third mixing vessel. Gycerin is added slowly to the third mixing vessel with mixing. Titanium dioxide is added to the third mixing vessel with mixing. The mixture in the third mixing vessel is then cooled to 45° C. with agitation. At 45° C., the agitation is stopped and the mixture in the third mixing vessel is cooled to room temperature. The oil continuous benefit phase is blended with structured surfactant phase at a specified ratio using a SpeedMixer™ (from FlackTek Inc.) at 2800 rpm for 1 min. Comparative Examples I and Inventive Examples 5 and 6 are subjected to the in-vitro deposition evaluation method, as described in the Test Methods above.

Comparative Example I and Inventive Examples 5 and 6 illustrate the importance of maintaining the ratio of hydrocarbon lipid to the low HLB emulsifier, as measured by the in-vitro deposition evaluation method. Comparative Example I comprises a oil continuous benefit phase with the ratio of hydrocarbon benefit material to low HLB emulsifier of 18:1 Inventive Examples 5 and 6 comprise a oil continuous benefit phase with the ratio of hydrocarbon lipid to low HLB emulsifier within the range of 30:1 to 200:1. The delta L values of Inventive Examples 5 and 6 are significantly higher than the comparative Example I. Further, inventive examples 5 and 6 show significantly better lather performance than comparative Example I. The inventive Examples also show significantly better lather performance versus Comparative Example I.

TABLE 6

Comparative Examples J and H and Inventive Example 7 and 8

|  | Comparative Examples | | Inventive Examples | |
| --- | --- | --- | --- | --- |
|  | J | K | 7 | 8 |
| I: Structured surfactant phase Composition | | | | |
| sodium trideceth sulfate, sulfated to >95% from ICONOL ™ TDA-3 tridecyl alcohol alkoxylate (BASF Corp.) | 8.5 | 8.5 | 8.5 | 8.5 |
| sodium lauryl sulfate (Procter & Gamble) | 8.5 | 8.5 | 8.5 | 8.5 |
| sodium lauroamphoacetate (Cognis Corp.) | 5 | 5 | 5 | 5 |
| guar hydroxypropyltrimonium chloride (JAGUAR ® Excel from Rhodia) | — | — | 0.6 | 0.6 |
| sodium chloride | 4.75 | 4.75 | 4.75 | 4.75 |
| trideceth-3 (ICONOL ™ TDA-3I from BASF Corp.) | 2 | 2 | 2 | 2 |
| methyl chloro isothiazolinone and methyl isothiazolinone (KATHON ™ CG from Rohm & Haas) | 0.033 | 0.033 | 0.033 | 0.033 |
| ethylenediaminetetraacetic acid (DISSOLVINE NA 2x from Akzo Nobel) | 0.15 | 0.15 | 0.15 | 0.15 |
| sodium benzoate | 0.2 | 0.2 | 0.2 | 0.2 |
| perfume | 1.8 | 1.8 | 1.8 | 1.8 |
| citric acid, titrated to a pH of | 5.7 ± 0.2 | 5.7 ± 0.2 | 5.7 ± 0.2 | 5.7 ± 0.2 |
| water and minors (NaOH) | Q.S. | Q.S. | Q.S. | Q.S. |
| II: Oil continuous benefit phase Composition | | | | |
| petrolatum (VERSAGEL ® P100 from Penereco) | 85.92 | 65.76 | 85.92 | 65.76 |
| glycerol monooleate, with an HLB of 3.8 (MONOMULS ® 90-0 18 from Cognis) | 0.48 | 1.44 | 0.48 | 1.44 |
| glycerin | 9.6 | 28.8 | 9.6 | 28.8 |
| titanium oxide (RBTD-834-11S2 from Kobo Products) | 4 | 4 | 4 | 4 |
| III: ratio of structured surfactant phase:oil continuous benefit phase blending ratio | 50:50 | 50:50 | 50:50 | 50:50 |
| IV: ratio of hydrocarbon benefit material:low HLB emulsifier | 179:1 | 45:1 | 179:1 | 45:1 |
| In-vitro Deposition of Comparative Examples J and K and Inventive Examples 7 and 8 | | | | |
| Delta L | 2.15 | 1.49 | 12.20 | 14.50 |
| Percent Difference of Delta L from Control | Control | −30% | +467% | +574% |

Comparative Examples J and K and Inventive Examples 7 and 8 are prepared by the following procedure: First, a citric solution is prepared by adding citric acid and distilled water into a first mixing vessel at a ratio of 50:50. In a second mixing vessel, add cationic polymer to water with agitation. Add sodium lauroamphoacetate, sodium lauryl sulfate, sodium trideceth sulfate, trideceth-3, sodium chloride, EDTA, sodium benzoate to the second mixing vessel. The pH of the mixture in the second mixing vessel is adjusted to 5.7±0.2 using the citric acid solution. Perfume and methyl chloro isothiazolinone and methyl isothiazolinone is added and mixed into the second mixing vessel until homogeneous forming the structured surfactant phase. The oil continuous benefit phase is prepared by adding petrolatum into a third mixing vessel while heating the third mixing vessel to about 88° C. Glyceryl monooleate is added to the third mixing vessel. Gycerin is added slowly to the third mixing vessel with mixing. Titanium dioxide is added to the third mixing vessel with mixing. The mixture in the third mixing vessel is then cooled to 45° C. with agitation. At 45° C., the agitation is stopped and the mixture in the third mixing vessel is cooled to room temperature. The oil continuous benefit phase is blended with structured surfactant phase at a specified ratio using a SpeedMixer™ (from FlackTek Inc.) at 2800 rpm for 1 min. Comparative Examples J and K and Inventive Examples 7 and 8 are subjected to the in-vitro deposition evaluation method, as described in the Test Methods above.

Comparative Examples J and K do not comprise a cationic deposition polymer in the structured surfactant phase. Inventive Example 7 and 8 comprise a cationic deposition polymer in the structured surfactant phase. From the difference in Delta L values compared by control, as measured by the in-vitro deposition evaluation method, it is evident that the Inventive Examples 7 and 8 deliver a significant increase in deposition utilizing a cationic deposition polymer, as compared to Comparative Examples J and K.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A multiphase personal care composition comprising:
   a. a structured surfactant phase comprising:
      i. from about 5% to about 30%, by weight of said multiphase personal care composition, of a mixture of lathering surfactants;
      ii. a lamellar inducing agent;
      iii. from about 0.1% to about 5%, by weight of the structured surfactant phase, of cationic guar hydroxypropyltrimonium chloride;
   b. an oil continuous benefit phase comprising:
      i. a hydrocarbon based benefit material;
      ii. a low HLB emulsifier comprising an unsaturated monoglyceryl ester having from about 14 to about 30 carbon atoms;
         wherein said benefit phase comprises a ratio of said hydrocarbon based benefit materials to said low HLB emulsifier comprising from about 30:1 to about 200:1.

2. The multiphase personal care composition of claim 1, wherein said structured surfactant phase comprises at least about 15% to about 22%, by weight of said multiphase personal care composition, of a mixture of lathering surfactants.

3. A multiphase personal care composition comprising:
   a. a structured surfactant phase comprising:
      i. from about 5% to about 30%, by weight of said multiphase personal care composition, of a mixture of lathering surfactants selected from anionic surfactants, nonionic surfactants, amphoteric surfactants, cationic surfactants, and mixtures thereof;
      ii. a lamellar phase inducing agent;
      iii. from about 0.5% to about 1%, by weight of the structured surfactant phase, of guar hydroxypropyltrimonium chloride;
   b. an oil continuous benefit phase comprising:
      i. a hydrocarbon based benefit material;
      ii. a low HLB emulsifier comprising an unsaturated monoglyceryl ester having from about 14 to about 30 carbon atoms;
         wherein said benefit phase comprises a ratio of said hydrocarbon based benefit materials to said low HLB emulsifier comprising from about 30:1 to about 200:1.

4. The multiphase personal care composition of claim 3, wherein said unsaturated monoglyceryl ester having from about 14 to about 30 carbon atoms comprises glycerol monooleate.

5. The multiphase personal care composition of claim 3, wherein said ratio of said hydrocarbon based benefit materials to said low HLB emulsifier comprises 95:1.

6. The multiphase personal care composition of claim 3, wherein the hydrocarbon based benefit material is selected from petrolatum, hydrocarbon oils, natural waxes, synthetic waxes, paraffins, ozokerite, polyethylene, polybutene, polydecene, pentahydrosqualene, and mixtures thereof.

7. A multiphase personal care composition comprising:
   a. a structured surfactant phase comprising:
      i. from about 15% to about 22%, by weight of said multiphase personal care composition, of a mixture of lathering surfactants selected from anionic surfactants, nonionic surfactants, and amphoteric surfactants;
      ii. a lamellar phase inducing agent comprising an electrolyte;
      iii. from about 01.% to about 5.0% by weight of the structured surfactant phase, guar hydroxypropyltrimonium chloride;
   b. an oil continuous benefit phase comprising:
      i. a hydrocarbon based benefit material selected from the group consisting of petrolatum, mineral oil, and mixtures thereof;
      ii. a low HLB emulsifier comprising glycerol monooleate;
         wherein said benefit phase has a ratio of said hydrocarbon based benefit materials to said low HLB emulsifier comprising from about 30:1 to about 200:1.

8. The multiphase personal care composition of claim 7, wherein the anionic surfactant comprises sodium trideceth sulfate.

9. The multiphase personal care composition of claim 7, wherein said amphoteric surfactant comprises sodium lauroamphoacetate.

10. The multiphase personal care composition of claim 7, wherein the structured surfactant phase comprises from about 0.1% to about 1%, by weight of the structured surfactant phase, of said guar hydroxypropyltrimonium chloride.

11. The multiphase personal care composition of claim 7, wherein said oil continuous benefit phase further comprises an additional low HLB emulsifier comprising an HLB of from about 1.5 to about 10.

12. The multiphase personal care composition of claim 7, further comprising an additional low HLB emulsifier selected from sorbitan monooleate, sorbitan stearate, trideceth-3, polyhydroxystearate, polyglyceryl-3 diisostearate, steareth-2, ceteth-2, propylene glycol isostearate, silicone copolyols, and mixtures thereof.

13. The multiphase personal care composition of claim 7, wherein said electrolyte is selected from sodium chloride, ammonium chloride, sodium sulfate, ammonium sulfate, and mixtures thereof.

14. The multiphase personal care composition of claim 7, wherein said multiphase personal care composition comprises from about 0.5 to about 5%, by weight of the structured surfactant phase, of electrolyte.

15. The multiphase personal care composition of claim 7, wherein said oil continuous benefit phase further comprises glycerin.

16. The multiphase personal care composition of claim 7, wherein said ratio of said hydrocarbon based benefit materials to said low HLB emulsifier comprises 49:1.

17. The multiphase personal care composition of claim 3, wherein the oil continuous benefit phase further comprises a second hydrophobic benefit material.

18. The composition of claim 1, wherein the composition comprises from about 0.5% to about 1%, by weight of the structured surfactant phase, of said cationic guar hydroxypropyltrimonium chloride.

19. The composition of claim 7, wherein the composition comprises from about 0.5% to about 1%, by weight of the structured surfactant phase, of said guar hydroxypropyltrimonium chloride.

* * * * *